(12) United States Patent
Chen

(10) Patent No.: US 10,426,718 B2
(45) Date of Patent: *Oct. 1, 2019

(54) COMPOSITIONS AND METHODS FOR TREATING HAIR LOSS AND DELAYING AGING OF SKIN

(71) Applicant: Phyto Tech Corp., Rancho Santa Margarita, CA (US)

(72) Inventor: Steven Chen, Rancho San Margarita, CA (US)

(73) Assignee: Phyto Tech Corp., Rancho Santa Margarita, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/481,492

(22) Filed: Apr. 7, 2017

(65) Prior Publication Data

US 2017/0216176 A1 Aug. 3, 2017

Related U.S. Application Data

(63) Continuation of application No. 14/414,428, filed as application No. PCT/US2013/050399 on Jul. 12, 2013.

(Continued)

(51) Int. Cl.
*A61K 9/00* (2006.01)
*A61K 8/49* (2006.01)
(Continued)

(52) U.S. Cl.
CPC ............ *A61K 8/498* (2013.01); *A61K 31/352* (2013.01); *A61K 36/72* (2013.01); *A61Q 5/02* (2013.01);
(Continued)

(58) Field of Classification Search
CPC ..................................................... A61K 8/498
See application file for complete search history.

(56) References Cited

U.S. PATENT DOCUMENTS 8,309,142 B1 * 11/2012 Vestevich ............... A61K 8/34
424/725
2006/0165636 A1 7/2006 Hasebe et al.
(Continued)

FOREIGN PATENT DOCUMENTS

CN 101485655 A 7/2009
CN 102225923 A 10/2011
(Continued)

OTHER PUBLICATIONS

International Search Report and Written Opinion dated Dec. 20, 2013 for International Application No. PCT/US2013/050399.
(Continued)

*Primary Examiner* — Paul W Dickinson
(74) *Attorney, Agent, or Firm* — Wolf, Greenfield & Sacks, P.C.; Karen K. Chan

(57) ABSTRACT

The invention provides methods of hair loss or inducing new hair growth, as well as methods of preventing hair loss, comprising applying an effective amount of a dihydromyricetin compound to the scalp. The invention also provides methods of delaying or reversing signs of aging skin comprising applying an effective amount of a dihydromyricetin compound to the skin. Also provided are cosmetic products (e.g., skin and hair products) comprising a dihydromyricetin compound and methods of making the same.

7 Claims, 3 Drawing Sheets

Related U.S. Application Data

(60) Provisional application No. 61/671,624, filed on Jul. 13, 2012.

(51) Int. Cl.
| | |
|---|---|
| *A61Q 7/00* | (2006.01) |
| *A61Q 19/08* | (2006.01) |
| *C07D 311/40* | (2006.01) |
| *A61K 31/352* | (2006.01) |
| *A61K 36/72* | (2006.01) |
| *A61Q 5/02* | (2006.01) |
| *A61Q 5/12* | (2006.01) |

(52) U.S. Cl.
CPC ............... *A61Q 5/12* (2013.01); *A61Q 7/00* (2013.01); *A61Q 19/08* (2013.01); *C07D 311/40* (2013.01); *A61K 2236/33* (2013.01); *A61K 2236/39* (2013.01); *A61K 2236/51* (2013.01); *A61K 2800/70* (2013.01)

(56) References Cited

U.S. PATENT DOCUMENTS

| | | |
|---|---|---|
| 2015/0209256 A1 | 7/2015 | Chen |
| 2017/0049674 A1 | 2/2017 | Chen |

FOREIGN PATENT DOCUMENTS

| | | |
|---|---|---|
| EP | 2 356 980 A2 | 8/2011 |
| JP | S63-208506 | 8/1988 |
| JP | 07-112916 | 5/1995 |
| JP | 2002-308790 | 10/2002 |
| JP | 2003-026584 | 1/2003 |
| WO | WO 2009/052518 | 4/2009 |

OTHER PUBLICATIONS

International Preliminary Report on Patentability dated Jan. 22, 2015 for International Application No. PCT/US2013/050399.

Extended European Search Report dated Dec. 23, 2015 for European Application No. EP 13817337.2.

Cacace et al., A flavonol O-methyltransferase from Catharanthus roseus performing two sequential methylations. Phytochemistry. Jan. 2003;62(2):127-37.

Cacace et al., A flavonol O-methyltransferase from Catharanthus roseus performing two sequential methylations. Phytochemistry. Jan. 2003;62(2):127-37. Erratum in: Phytochemistry. May 2003;63(2):237.

Ding et al., [Study on flavonoids in seeds of Hovenia dulcis]. Yao Xue Xue Bao. Aug. 1997;32(8):600-2. Chinese.

Du et al., Purification of (+)-dihydromyricetin from leaves extract of Ampelopsis grossedentata using high-speed countercurrent chromatograph with scale-up triple columns. J Chromatogr A. Oct. 11, 2002;973(1-2):217-20.

Fernandez-Vozmediano et al., Contact dermatitis due to topical spironolactone. Contact Dermatitis. Feb. 1994;30(2):118-9.

Gan et al., Prevalence of male and female pattern hair loss in Maryborough. J Investig Dermatol Symp Proc. Dec. 2005;10(3):184-9.

Jeon et al., Cytotoxic constituents from the bark of Salix hulteni. Arch Pharm Res. Aug. 2008;31(8):978-82. doi:10.1007/s12272-001-1255-9. Epub Sep. 12, 2008.

Li et al., Comparison of refluxing, ultrasonic- and microwave-assisted extraction of dihydromyricetin from Ampelopsis grossedentata. J AOAC Int. Nov.-Dec. 2008;91(6):1278-83.

Louis et al., Phytochemical characterization of Rhododendron ferrugineum and in vitro assessment of an aqueous extract on cell toxicity. Planta Med. Oct. 2010;76(14):1550-7. doi: 10.1055/s-0029-1241016. Epub Mar. 22, 2010.

Ma et al., Bioactive novel polyphenols from the fruit of *Manilkara zapota* (Sapodilla). J Nat Prod. Jul. 2003;66(7):983-6.

Nazemiyeh et al., Antioxidant phenolic compounds from the leaves of *Erica arborea* (Ericaceae). Nat Prod Res. 2008;22(16):1385-92. doi: 10.1080/14786410701824007.

Ni et al., [Studies on the chemical constituents of Xanthoceras sorbifolia]. Zhong Yao Cai. May 2009;32(5):702-4. Chinese.

Stafford et al., Flavan-3-ol Biosynthesis : The Conversion of (+)-Dihydromyricetin to Its Flavan-3,4-Diol (Leucodelphinidin) and to (+)-Gallocatechin by Reductases Extracted from Tissue Cultures of Ginkgo biloba and Pseudotsuga menziesii. Plant Physiol. Aug. 1985;78(4):791-4.

Towatari et al., Polyphenols from the heartwood of Cercidiphyllum japonicum and their effects on proliferation of mouse hair epithelial cells. Planta Med. Nov. 2002;68(11):995-8.

Tresch et al., T cell-mediated acute localized exanthematous pustulosis caused by finasteride. J Allergy Clin Immunol. Feb. 2012;129(2):589-94. doi:10.1016/j.jaci.2011.07.033. Epub Aug. 24, 2011.

Uno et al., Action of topical minoxidil in the bald stump-tailed macaque. J Am Acad Dermatol. Mar. 1987;16(3 Pt 2):657-68.

Yin et al., New galloylated flavanonols from the Australian plant *Glochidion sumatranum*. Planta Med. Nov. 2010;76(16):1877-81. doi: 10.1055/s-0030-1250071. Epub Jul. 1, 2010.

Yoo et al., Recovery and pre-purification of (+)-dihydromyricetin from Hovenia dulcis. Process Biochemistry. Mar. 2006;41(3):567-70.

\* cited by examiner

COMPOSITIONS AND METHODS FOR TREATING HAIR LOSS AND DELAYING AGING OF SKIN

CROSS-REFERENCE TO RELATED APPLICATIONS

This application is a continuation application of U.S. application Ser. No. 14/414,428, filed Jan. 12, 2015, which is a 35 U.S.C. § 371 National Phase Application of International Application No. PCT/US2013/050399, filed Jul. 12, 2013, which claims the benefit of U.S. Provisional Application No. 61/671,624 filed Jul. 13, 2012, the disclosure of each of which is hereby incorporated by reference in their entirety.

FIELD OF THE INVENTION

This invention relates to compositions and methods to treat hair loss, promote hair growth, or delay or reverse the signs of aging skin, and methods of making related products.

BACKGROUND OF THE INVENTION

Hair loss is a common problem that affects men and women of all ages throughout the world. One large-scale study in Maryborough, Victoria, Australia, showed the prevalence of mid-frontal hair loss increases with age and affects 73.5% of men and 57% of women aged 80 and over (Gan et al. (2005) "Prevalence of male and female pattern hair loss in Maryborough." *J Investig Dermatol Symp Proc.* 10:184-189). According to Medem Medical Library's website, male pattern hair loss or baldness (MPB) affects about 40 million men in the United States. Approximately 25% of men begin balding by age 30; two-thirds begin balding by age 60.

Hair growth typically follows a continuously repeating cycle related to rest, shedding, and regrowth. However, a variety of factors, including hormonal changes, poor nutrition, illness, medications, and stress, can disrupt this cycle and lead to excessive hair loss, thinning hair, or baldness. For example, the hormone dihydrotestosterone or DHT is widely accepted to be the main cause of male pattern baldness. Thyroid disease, diabetes, and lupus frequently cause general hair loss. Stress can aggravate alopecia areata, which is characterized by the sudden loss of hair in round or oval patches about the size of a quarter. A second form stress-induced hair loss is telogen effluvium (TE), which occurs when a sudden or severe stress causes an acute increase in the shedding of hair.

Currently available hair loss treatments have been shown to be moderately successful in renewing hair growth. However, medications for the treatment of hair loss, such as minoxidil, procaine, and finasteride, can comprise pharmaceutical agents that cause undesirable side effects, including irritation, severe allergic reactions, and an increased risk of prostate cancer in men. Finasteride also poses significant danger to women of childbearing age and should not be handled by pregnant women. Moreover, surgical procedures can be expensive, painful, and can carry the risk of complications, such as infection, scarring, or unnatural appearance of the direction of hair growth.

What is needed is a safe, effective, natural treatment that can be administered topically to prevent and/or reverse hair loss or induce new hair growth.

All references cited herein, including patent applications and publications, are hereby incorporated by reference in their entirety.

BRIEF SUMMARY OF THE INVENTION

In one aspect, the invention provides a method for treating hair loss or inducing hair growth (such as new hair growth) comprising applying an effective amount of a dihydromyricetin compound to scalp of an individual, wherein the dihydromyricetin compound is of formula (I):

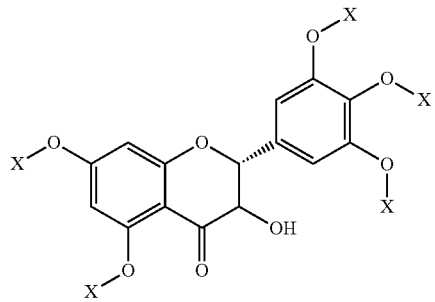

wherein each X is independently selected from hydrogen, alkyl, substituted alkyl, alkenyl, substituted alkenyl, halo, alkoxyl, heteroalkyl, substituted heteroalkyl, heteroalkenyl, or substituted heteroalkenyl, or a salt thereof. In some embodiments, the X is hydrogen (i.e., the dihydromyricetin compound is dihydromyricetin). In some embodiments, the X is independently selected from the group consisting of —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —CH$_2$C(CH$_3$)$_2$CH$_3$, —C(CH$_3$)$_2$CH$_2$CH$_3$, —CH$_2$CH$_2$CH(CH$_3$)$_2$, —CH$_2$CH$_2$CH$_2$CH$_2$CH$_2$CH$_3$, —CH$_2$C(CH$_3$)$_2$CH$_2$CH$_3$, —CH$_2$CH$_2$C(CH$_3$)$_2$CH$_3$, —CH$_2$CH$_2$CH$_2$CH(CH$_3$)$_2$, —CH$_2$CH(CH$_2$CH$_3$)CH$_2$CH$_3$, —CH$_2$CH$_2$OCH$_3$, —CH$_2$CH$_2$CH$_2$OCH$_3$, —CH$_2$CH$_2$CH$_2$OCH$_2$CH$_3$, and —CH$_2$CH$_2$CH$_2$CH$_2$OCH$_2$CH$_3$. In some embodiments, the dihydromyricetin compound is of formula (II):

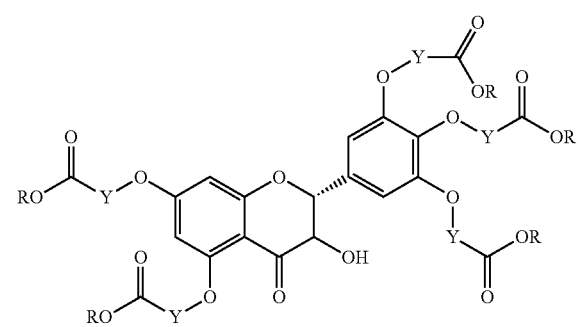

wherein each Y is independently selected from is C$_{1-12}$ alkylene or C$_{1-12}$ alkenylene, and wherein each R is independently C$_{1-12}$ alkyl, or a salt thereof.

In some embodiments, the dihydromyricetin compound is of formula (III):

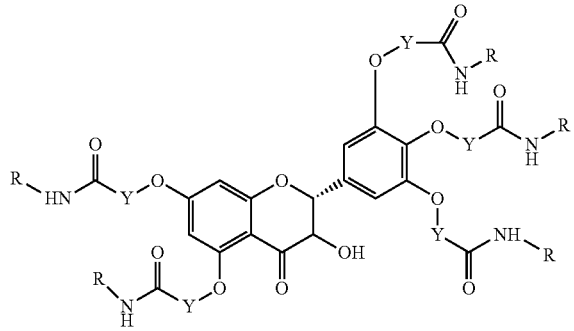

wherein each Y is independently selected from is $C_{1-12}$ alkylene or $C_{1-12}$ alkenylene, and wherein each R is independently $C_{1-12}$ alkyl, or a salt thereof.

In some embodiments, the dihydromyricetin compound is provided in a hair product (e.g., a shampoo, a conditioner, or a hair spray, etc.). In some embodiments, the dihydromyricetin compound in the hair product is in a concentration of at least about 5% (w/v-%) or at least about 5% (w/w-%). In some embodiments, the dihydromyricetin compound in the hair product is in a concentration of at least about 10% (w/v-%) or at least about 10% (w/w-%).

In another aspect, the invention provides a method for preventing hair loss comprising applying an effective amount of a dihydromyricetin compound to scalp of an individual, wherein the dihydromyricetin compound is of formula (I):

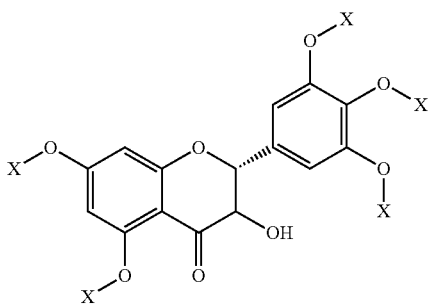

wherein X is hydrogen, alkyl, substituted alkyl, alkenyl, substituted alkenyl, halo, alkoxyl, heteroalkyl, substituted heteroalkyl, heteroalkenyl, or substituted heteroalkenyl, or a salt thereof. In some embodiments, the X is hydrogen (i.e., the dihydromyricetin compound is dihydromyricetin). In some embodiments, the X is independently selected from the group consisting of —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, —$CH_2CH_2CH_2CH_2CH_3$, —$CH_2C(CH_3)_2CH_3$, —$C(CH_3)_2CH_2CH_3$, —$CH_2CH_2CH(CH_3)_2$, —$CH_2CH_2CH_2CH_2CH_2CH_3$, —$CH_2C(CH_3)_2CH_2CH_3$, —$CH_2CH_2C(CH_3)_2CH_3$, —$CH_2CH_2CH_2CH(CH_3)_2$, —$CH_2CH(CH_2CH_3)CH_2CH_3$, —$CH_2CH_2OCH_3$, —$CH_2CH_2CH_2OCH_3$, —$CH_2CH_2CH_2OCH_2CH_3$, and —$CH_2CH_2CH_2CH_2OCH_2CH_3$. In some embodiments, the dihydromyricetin compound is of formula (II):

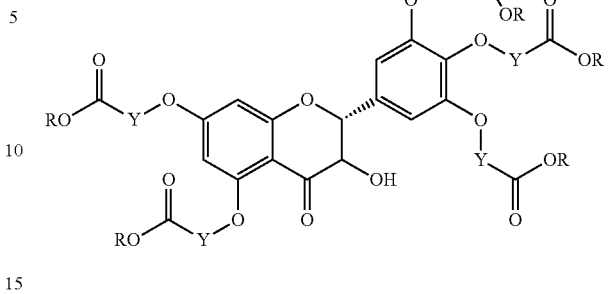

wherein each Y is independently selected from is $C_{1-12}$ alkylene or $C_{1-12}$ alkenylene, and wherein each R is independently $C_{1-12}$ alkyl, or a salt thereof.

In some embodiments, the dihydromyricetin compound is of formula (III):

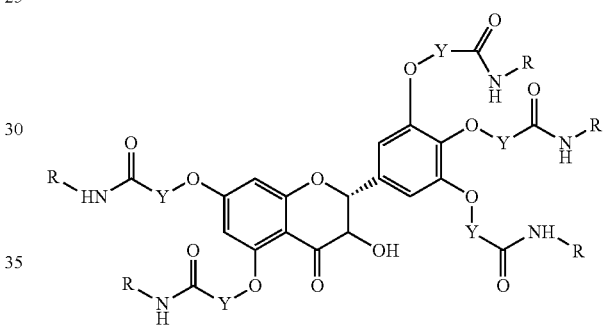

wherein each Y is independently selected from is $C_{1-12}$ alkylene or $C_{1-12}$ alkenylene, and wherein each R is independently $C_{1-12}$ alkyl, or a salt thereof.

In some embodiments of the methods described above, the dihydromyricetin compound is provided in a hair product (e.g., a shampoo, a conditioner, or a hair spray, etc.). In some embodiments, the dihydromyricetin compound in the hair product is in a concentration of about 0.01 μM to about 250 μM. In some embodiments, the dihydromyricetin compound in the hair product is in a concentration of about 0.5 μM to about 10 μM. In some embodiments, the dihydromyricetin compound is synthetic or extracted and purified from a whole plant or a plant tissue of *Hovenia dulcis, Leptarrhena pyrolifolia, Pinus contorta, Ampelopsis grossedentata, Glochidion sumatranum, Rhododendron ferrugineum, Erica arborea, Salix hulteni, Manilkara zapota, Catharanthus roseus, Myrica rubra*, or *Xanihoceras sorbifolia*.

In some embodiments of the methods described above, the individual is a human. In some embodiments, the individual has chronic stress, alopecia, and/or baldness.

In another aspect, the invention provides a method for delaying or reversing signs of aging skin comprising applying an effective amount of a dihydromyricetin compound to the skin of an individual, wherein the dihydromyricetin compound is of formula (I):

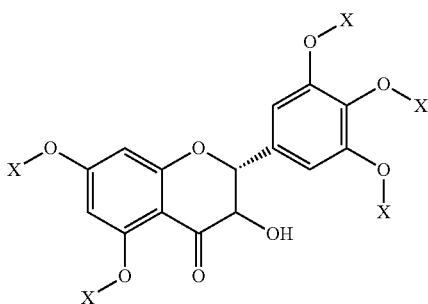

wherein each X is independently selected from hydrogen, alkyl, substituted alkyl, alkenyl, substituted alkenyl, halo, alkoxyl, heteroalkyl, substituted heteroalkyl, heteroalkenyl, or substituted heteroalkenyl, or a salt thereof. In some embodiments, the X is hydrogen (i.e., the dihydromyricetin compound is dihydromyricetin). In some embodiments, the X is independently selected from the group consisting of —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —CH$_2$C(CH$_3$)$_2$CH$_3$, —C(CH$_3$)$_2$CH$_2$CH$_3$, —CH$_2$CH$_2$CH(CH$_3$)$_2$, —CH$_2$CH$_2$CH$_2$CH$_2$CH$_2$CH$_3$, —CH$_2$C(CH$_3$)$_2$CH$_2$CH$_3$, —CH$_2$CH$_2$C(CH$_3$)$_2$CH$_3$, —CH$_2$CH$_2$CH$_2$CH(CH$_3$)$_2$, —CH$_2$CH(CH$_2$CH$_3$)CH$_2$CH$_3$, —CH$_2$CH$_2$OCH$_3$, —CH$_2$CH$_2$CH$_2$OCH$_3$, —CH$_2$CH$_2$CH$_2$OCH$_2$CH$_3$, and —CH$_2$CH$_2$CH$_2$CH$_2$OCH$_2$CH$_3$. In some embodiments, the dihydromyricetin compound is of formula (II):

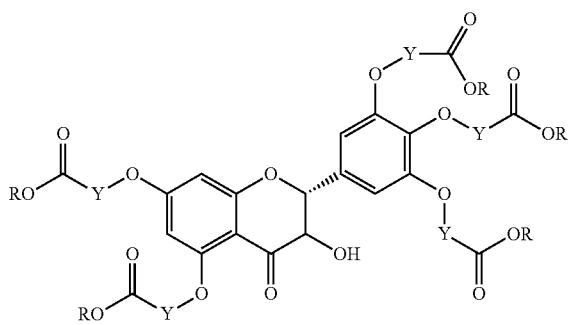

wherein each Y is independently selected from is C$_{1-12}$ alkylene or C$_{1-12}$ alkenylene, and wherein each R is independently C$_{1-12}$ alkyl, or a salt thereof.

In some embodiments, the dihydromyricetin compound is of formula (III):

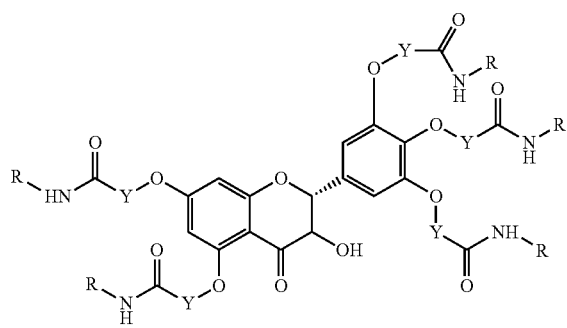

wherein each Y is independently selected from is C$_{1-12}$ alkylene or C$_{1-12}$ alkenylene, and wherein each R is independently C$_{1-12}$ alkyl, or a salt thereof.

In some embodiments, the dihydromyricetin compound is extracted and purified from a whole plant or a plant tissue of *Hovenia dulcis*, *Leptarrhena pyrolifolia*, *Pinus contorta*, *Ampelopsis grossedentata*, *Glochidion sumatranum*, *Rhododendron ferrugineum*, *Erica arborea*, *Salix hulteni*, *Manilkara zapota*, *Catharanthus roseus*, or *Xanthoceras sorbifolia*.

In some embodiments, the dihydromyricetin compound is provided in a skin product (e.g., a moisturizer, a facial polisher, a facial cleaner, a sunscreen, or a skin patch, etc.). In some embodiments, the dihydromyricetin compound in the skin product is in a concentration of about 0.01 μM to about 250 μM. In some embodiments, the dihydromyricetin compound in the skin product is in a concentration of about 0.5 μM to about 10 μM. In some embodiments, the dihydromyricetin compound in the skin product is in a concentration of at least about 5% (w/v-%) or at least about 5% (w/w-%). In some embodiments, the dihydromyricetin compound in the skin product is in a concentration of at least about 10% (w/v-%) or at least about 10% (w/w-%).

In some embodiments, the individual is a human. In some embodiments, the individual has chronic stress. In some embodiments, the individual has skin rash, skin dehydration, or psycho-emotional changes associated with chronic stress.

In another aspect, the invention provides a cosmetic product comprising a dihydromyricetin compound or a salt thereof, wherein the dihydromyricetin compound is of formula (I):

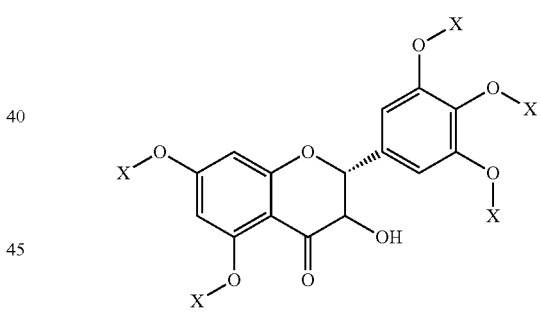

wherein each X is independently selected from hydrogen, alkyl, substituted alkyl, alkenyl, substituted alkenyl, halo, alkoxyl, heteroalkyl, substituted heteroalkyl, heteroalkenyl, or substituted heteroalkenyl, and wherein said dihydromyricetin in the product is at least about 0.01 μM. In some embodiments, the X is hydrogen (i.e., the dihydromyricetin compound is dihydromyricetin). In some embodiments, the X is independently selected from the group consisting of —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —CH$_2$C(CH$_3$)$_2$CH$_3$, —C(CH$_3$)$_2$CH$_2$CH$_3$, —CH$_2$CH$_2$CH(CH$_3$)$_2$, —CH$_2$CH$_2$CH$_2$CH$_2$CH$_2$CH$_3$, —CH$_2$C(CH$_3$)$_2$CH$_2$CH$_3$, —CH$_2$CH$_2$C(CH$_3$)$_2$CH$_3$, —CH$_2$CH$_2$CH$_2$CH(CH$_3$)$_2$, —CH$_2$CH(CH$_2$CH$_3$)CH$_2$CH$_3$, —CH$_2$CH$_2$OCH$_3$, —CH$_2$CH$_2$CH$_2$OCH$_3$, —CH$_2$CH$_2$CH$_2$OCH$_2$CH$_3$, and —CH$_2$CH$_2$CH$_2$CH$_2$OCH$_2$CH$_3$. In some embodiments, the dihydromyricetin compound is of formula (II):

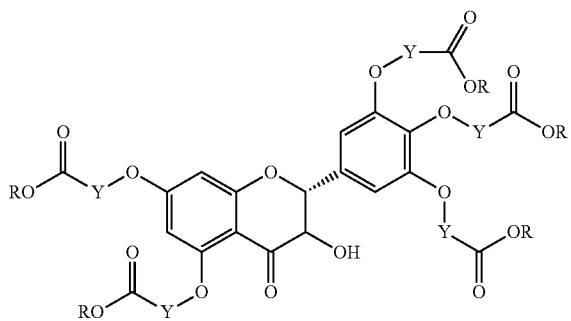

wherein each Y is independently selected from is $C_{1-12}$ alkylene or $C_{1-12}$ alkenylene, and wherein each R is independently $C_{1-12}$ alkyl, or a salt thereof.

In some embodiments, the dihydromyricetin compound is of formula (III):

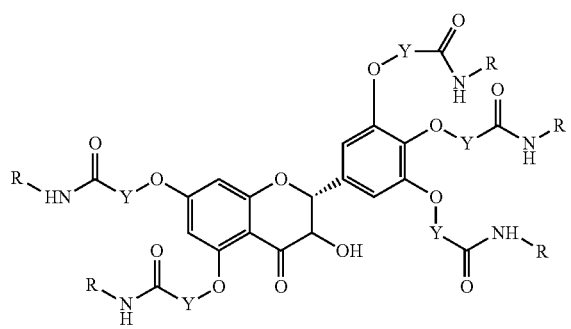

wherein each Y is independently selected from is $C_{1-12}$ alkylene or $C_{1-12}$ alkenylene, and wherein each R is independently $C_{1-12}$ alkyl, or a salt thereof.

In some embodiments, the dihydromyricetin compound in the product is about 0.01 µM to about 250 µM. In some embodiments, the dihydromyricetin compound in the product is about 0.5 µM to about 10 µM.

In another aspect, the invention provides a cosmetic product comprising a dihydromyricetin compound or a salt thereof, wherein the dihydromyricetin compound is of formula (I):

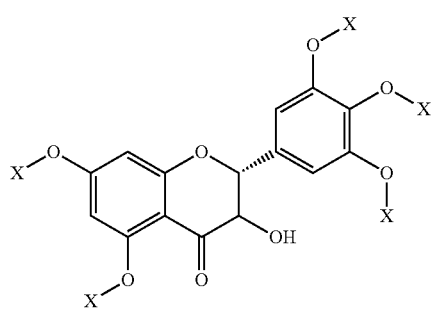

wherein each X is independently selected from hydrogen, alkyl, substituted alkyl, alkenyl, substituted alkenyl, halo, alkoxyl, heteroalkyl, substituted heteroalkyl, heteroalkenyl, or substituted heteroalkenyl, and wherein purified dihydromyricetin has been added to the cosmetic product or a material from which the cosmetic product is made. In some embodiments, the X is hydrogen (i.e., the dihydromyricetin compound is dihydromyricetin). In some embodiments, the X is independently selected from the group consisting of —CH₃, —CH₂CH₃, —CH₂CH₂CH₃, —CH(CH₃)₂, —CH₂CH₂CH₂CH₃, —CH₂CH(CH₃)₂, —C(CH₃)₃, —CH₂CH₂CH₂CH₂CH₃, —CH₂C(CH₃)₂CH₃, —C(CH₃)₂CH₂CH₃, —CH₂CH₂CH(CH₃)₂, —CH₂CH₂CH₂CH₂CH₃, —CH₂C(CH₃)₂CH₂CH₃, —CH₂CH₂C(CH₃)₂CH₃, —CH₂CH₂CH₂CH(CH₃)₂, —CH₂CH(CH₂CH₃)CH₂CH₃, —CH₂CH₂OCH₃, —CH₂CH₂CH₂OCH₃, —CH₂CH₂CH₂OCH₂CH₃, and —CH₂CH₂CH₃CH₂OCH₂CH₃. In some embodiments, the dihydromyricetin compound is of formula (II):

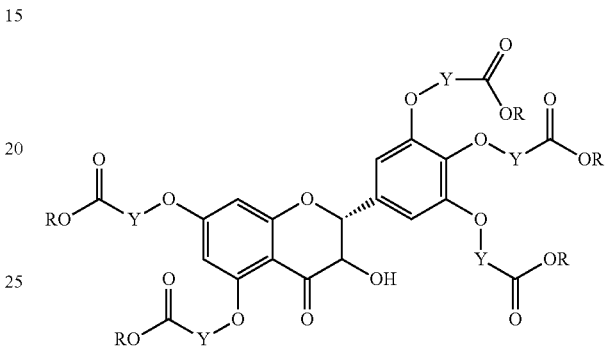

wherein each Y is independently selected from is $C_{1-12}$ alkylene or $C_{1-12}$ alkenylene, and wherein each R is independently $C_{1-12}$ alkyl, or a salt thereof.

In some embodiments, the dihydromyricetin compound is of formula (III):

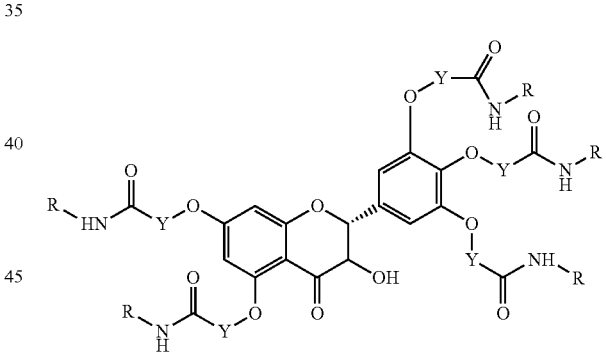

wherein each Y is independently selected from is $C_{1-12}$ alkylene or $C_{1-12}$ alkenylene, and wherein each R is independently $C_{1-12}$ alkyl, or a salt thereof.

In some embodiments of the cosmetic product described above, the dihydromyricetin compound is synthetic or extracted and purified from a whole plant or a plant tissue of Hovenia dulcis, Leptarrhena pyrolifolia, Pinus contorta, Ampelopsis grossedentata, Glochidion sumatranum, Rhododendron ferrugineum, Erica arborea, Salix hulteni, Manilkara zapota, Catharanthus roseus, Myrica rubra, or Xanthoceras sorbifolia and added to the cosmetic product or the material from which the cosmetic product is made. In some embodiments of the cosmetic product described above, the purified dihydromyricetin compound is at least about 90% pure, at least about 95% pure, at least about 98% pure, or at least about 99% pure.

In some embodiments of the cosmetic product described above, the cosmetic product is a hair product (e.g., a shampoo, a conditioner, or a hair spray, etc.). In some embodiments of the cosmetic product described above, the cosmetic product is a skin product (e.g., a moisturizer, a facial polisher, a facial cleaner, a sunscreen, or a skin patch, etc.).

In another aspect, the invention provides a method of making a cosmetic product comprising adding a dihydromyricetin compound or a salt thereof to a cosmetic product or a material from which the cosmetic product is made, wherein the dihydromyricetin compound is of formula (I):

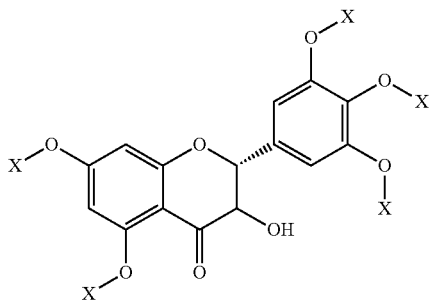

wherein each X is independently selected from hydrogen, alkyl, substituted alkyl, alkenyl, substituted alkenyl, halo, alkoxyl, heteroalkyl, substituted heteroalkyl, heteroalkenyl, or substituted heteroalkenyl, and wherein the final concentration of the dihydromyricetin compound in the cosmetic product is at least about 0.01 µM. In some embodiments, the X is hydrogen (i.e., the dihydromyricetin compound is dihydromyricetin). In some embodiments, the X is independently selected from the group consisting of —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —CH$_2$C(CH$_3$)$_2$CH$_3$, —C(CH$_3$)$_2$CH$_2$CH$_3$, —CH$_2$CH$_2$CH(CH$_3$)$_2$, —CH$_2$CH$_2$CH$_2$CH$_2$CH$_2$CH$_3$, —CH$_2$C(CH$_3$)$_2$CH$_2$CH$_3$, —CH$_2$CH$_2$C(CH$_3$)$_2$CH$_3$, —CH$_2$CH$_2$CH$_2$CH(CH$_3$)$_2$, —CH$_2$CH(CH$_2$CH$_3$)CH$_2$CH$_3$, —CH$_2$CH$_2$OCH$_3$, —CH$_2$CH$_2$CH$_2$OCH$_3$, —CH$_2$CH$_2$CH$_2$OCH$_2$CH$_3$, and —CH$_2$CH$_2$CH$_2$CH$_2$OCH$_2$CH$_3$. In some embodiments, the dihydromyricetin compound is of formula (II):

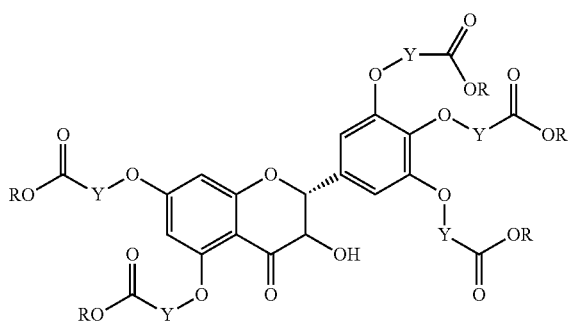

wherein each Y is independently selected from is C$_{1-12}$ alkylene or C$_{1-12}$ alkenylene, and wherein each R is independently C$_{1-12}$ alkyl, or a salt thereof.

In some embodiments, the dihydromyricetin compound is of formula (III):

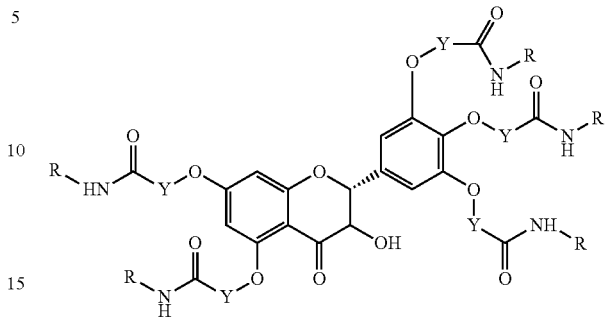

wherein each Y is independently selected from is C$_{1-12}$ alkylene or C$_{1-12}$ alkenylene, and wherein each R is independently C$_{1-12}$ alkyl, or a salt thereof.

In some embodiments, the final concentration of the dihydromyricetin compound in the cosmetic product is about 0.01 µM to about 250 µM. In some embodiments, the final concentration of the dihydromyricetin compound in the cosmetic product is about 0.5 µM to about 10 µM.

In another aspect, the invention provides a method of making a cosmetic product comprising adding a purified dihydromyricetin compound or a salt thereof to a cosmetic product or a material from which the cosmetic product is made, wherein the dihydromyricetin compound is of formula (I):

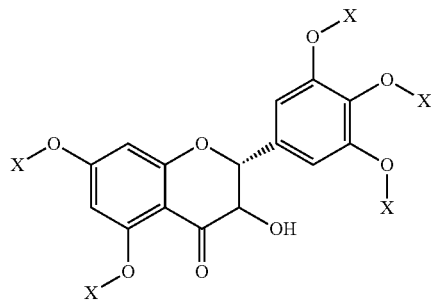

wherein each X is independently selected from hydrogen, alkyl, substituted alkyl, alkenyl, substituted alkenyl, halo, alkoxyl, heteroalkyl, substituted heteroalkyl, heteroalkenyl, or substituted heteroalkenyl, and wherein the final concentration of the dihydromyricetin compound in the cosmetic product is at least about 0.01 µM. In some embodiments, the X is hydrogen (i.e., the dihydromyricetin compound is dihydromyricetin). In some embodiments, the X is independently selected from the group consisting of —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —CH$_2$C(CH$_3$)$_2$CH$_3$, —C(CH$_3$)$_2$CH$_2$CH$_3$, —CH$_2$CH$_2$CH(CH$_3$)$_2$, —CH$_2$CH$_2$CH$_2$CH$_2$CH$_2$CH$_3$, —CH$_2$C(CH$_3$)$_2$CH$_2$CH$_3$, —CH$_2$CH$_2$C(CH$_3$)$_2$CH$_3$, —CH$_2$CH$_2$CH$_2$CH(CH$_3$)$_2$, —CH$_2$CH(CH$_2$CH$_3$)CH$_2$CH$_3$, —CH$_2$CH$_2$OCH$_3$, —CH$_2$CH$_2$CH$_2$OCH$_3$, —CH$_2$CH$_2$CH$_2$OCH$_2$CH$_3$, and —CH$_2$CH$_2$CH$_2$CH$_2$OCH$_2$CH$_3$. In some embodiments, the dihydromyricetin compound is of formula (II):

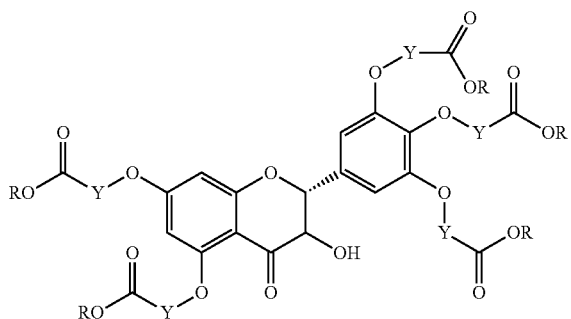

wherein each Y is independently selected from is $C_{1-12}$ alkylene or $C_{1-12}$ alkenylene, and wherein each R is independently $C_{1-12}$ alkyl, or a salt thereof.

In some embodiments, the dihydromyricetin compound is of formula (III):

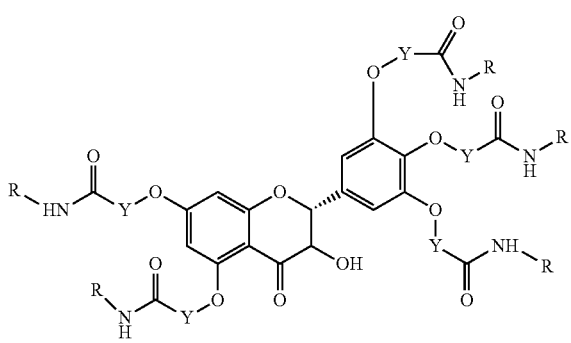

wherein each Y is independently selected from is $C_{1-12}$ alkylene or $C_{1-12}$ alkenylene, and wherein each R is independently $C_{1-12}$ alkyl, or a salt thereof.

In some embodiments of the method of making a cosmetic product described above, the dihydromyricetin compound is synthetic or extracted and purified from a whole plant or a plant tissue of Hovenia *dulcis, Leptarrhena pyrolifolia, Pinus contorta, Ampelopsis grossedentata, Glochidion sumatranum, Rhododendron ferrugineum, Erica arborea, Salix hulteni, Manilkara zapota, Catharanthus roseus, Myrica rubra,* or *Xanthoceras sorbifolia*. In some embodiments, the purified dihydromyricetin compound is at least about 90% pure, at least about 95% pure, at least about 98% pure, or at least about 99% pure.

In some embodiments of the method of making a cosmetic product described above, the cosmetic product is a hair product (e.g., a shampoo, a conditioner, or a hair spray, etc.). In some embodiments of the method of making a cosmetic product described above, the cosmetic product is a skin product (e.g., a moisturizer, a facial polisher, a facial cleaner, a sunscreen, or a skin patch, etc.).

In another aspect, the invention provides a method of extracting and purifying dihydromyricetin from a whole plant or a plant tissue comprising the steps of (a) extracting a whole plant or a plant tissue that contains dihydromyricetin with a first ethanol water solution; (b) concentrating and crystalizing compounds in the extract of step (a); (c) re-extracting the crystalized compounds with a second ethanol water solution; and (d) concentrating and crystalizing compounds in the extract of step (c), wherein the crystalized material in step (d) contains purified dihydromyricetin. In some embodiments, the first ethanol water solution contains about 60% to about 80% ethanol (such as about 70% ethanol). In some embodiments, the second ethanol water solution contains about 70% to about 90% ethanol (such as about 80% ethanol). In some embodiments, the extraction is from a whole plant or a plant tissue of *Hovenia dulcis, Leptarrhena pyrolifolia, Pinus contorta, Ampelopsis grossedentata, Glochidion sumatranum, Rhododendron ferrugineum, Erica arborea, Salix hulteni, Manilkara zapota, Catharanthus roseus, Myrica rubra,* or *Xanthoceras sorbifolia*. In some embodiments, the crystalized material in step (d) contains at least 95% or at least 98% dihydromyricetin.

In another aspect, the invention provides kits or articles of manufacture comprising (a) a composition comprising a dihydromyricetin compound, wherein the dihydromyricetin compound is of formula (I):

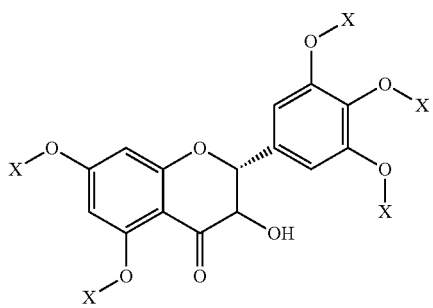

wherein each X is independently selected from hydrogen, alkyl, substituted alkyl, alkenyl, substituted alkenyl, halo, alkoxyl, heteroalkyl, substituted heteroalkyl, heteroalkenyl, or substituted heteroalkenyl, or a salt thereof and (b) a package insert or a label indicating that the product is useful for promoting hair growth, reversing hair loss (or balding), promoting natural hair regrowth, increasing the thickness of thin (or thinning) hair, or preventing hair loss (or balding). In some embodiments, the X is hydrogen (i.e., the dihydromyricetin compound is dihydromyricetin). In some embodiments, the X is independently selected from the group consisting of $-CH_3$, $-CH_2CH_3$, $-CH_2CH_2CH_3$, $-CH(CH_3)_2$, $-CH_2CH_2CH_2CH_3$, $-CH_2CH(CH_3)_2$, $-C(CH_3)_3$, $-CH_2CH_2CH_2CH_2CH_3$, $-CH_2C(CH_3)_2CH_3$, $-C(CH_3)_2CH_2CH_3$, $-CH_2CH_2CH(CH_3)_2$, $-CH_2CH_2CH_2CH_2CH_2CH_3$, $-CH_2C(CH_3)_2CH_2CH_3$, $-CH_2CH_2C(CH_3)_2CH_3$, $-CH_2CH_2CH_2CH(CH_3)_2$, $-CH_2CH(CH_2CH_3)CH_2CH_3$, $-CH_2CH_2OCH_3$, $-CH_2CH_2CH_2OCH_3$, $-CH_2CH_2CH_2OCH_2CH_3$, and $-CH_2CH_2CH_2CH_2OCH_2CH_3$. In some embodiments, the dihydromyricetin compound is of formula (II):

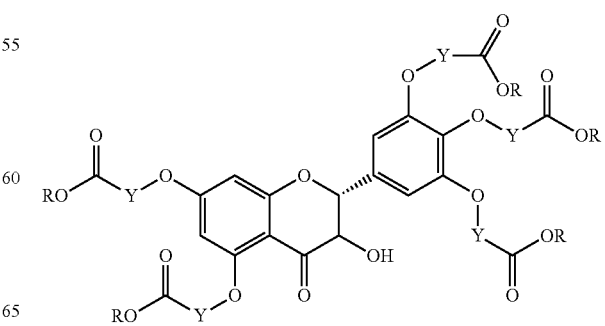

wherein each Y is independently selected from is $C_{1-12}$ alkylene or $C_{1-12}$ alkenylene, and wherein each R is independently $C_{1-12}$ alkyl, or a salt thereof.

In some embodiments, the dihydromyricetin compound is of formula (III):

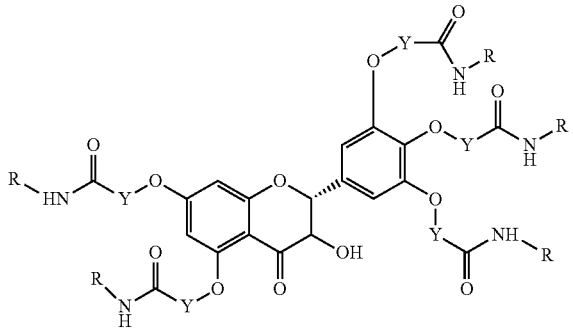

wherein each Y is independently selected from is $C_{1-12}$ alkylene or $C_{1-12}$ alkenylene, and wherein each R is independently $C_{1-12}$ alkyl, or a salt thereof.

In another aspect, the invention provides kits or articles of manufacture comprising (a) a composition comprising a dihydromyricetin compound, wherein the dihydromyricetin compound is of formula (I):

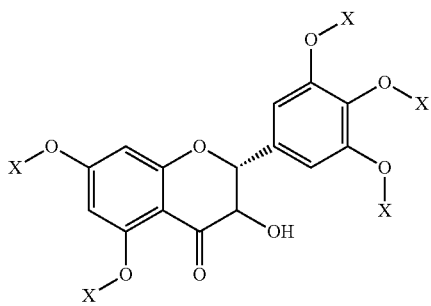

wherein each X is independently selected from hydrogen, alkyl, substituted alkyl, alkenyl, substituted alkenyl, halo, alkoxyl, heteroalkyl, substituted heteroalkyl, heteroalkenyl, or substituted heteroalkenyl, or a salt thereof; and (b) a package insert or a label indicating that the product is useful for delaying skin aging or reversing the signs of skin aging. In some embodiments, the X is hydrogen (i.e., the dihydromyricetin compound is dihydromyricetin). In some embodiments, the X is independently selected from the group consisting of —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, —$CH_2CH_2CH_2CH_2CH_3$, —$CH_2C(CH_3)_2CH_3$, —$C(CH_3)_2CH_2CH_3$, —$CH_2CH_2CH(CH_3)_2$, —$CH_2CH_2CH_2CH_2CH_2CH_3$, —$CH_2C(CH_3)_2CH_2CH_3$, —$CH_2CH_2C(CH_3)_2CH_3$, —$CH_2CH_2CH_2CH(CH_3)_2$, —$CH_2CH(CH_2CH_3)CH_2CH_3$, —$CH_2CH_2OCH_3$, —$CH_2CH_2CH_2OCH_3$, —$CH_2CH_2CH_2OCH_2CH_3$, and —$CH_2CH_2CH_2CH_2OCH_2CH_3$. In some embodiments, the dihydromyricetin compound is of formula (II):

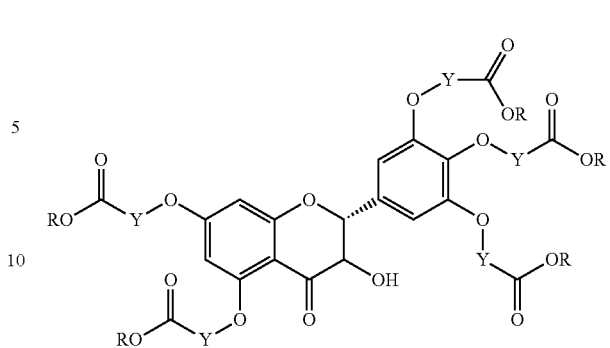

wherein each Y is independently selected from is $C_{1-12}$ alkylene or $C_{1-12}$ alkenylene, and wherein each R is independently $C_{1-12}$ alkyl, or a salt thereof.

In some embodiments, the dihydromyricetin compound is of formula (III):

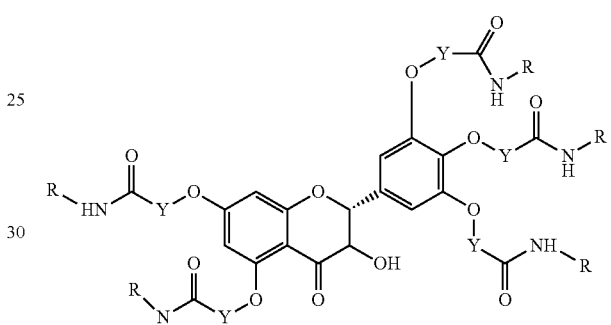

wherein each Y is independently selected from is $C_{1-12}$ alkylene or $C_{1-12}$ alkenylene, and wherein each R is independently $C_{1-12}$ alkyl, or a salt thereof.

In some embodiments, the composition comprising the dihydromyricetin compound is a cosmetic product. In some embodiments, the composition comprising the dihydromyricetin compound is packaged in a container with the insert or a label. In some embodiments, the label further indicates that the product has a stress reducing, calming, and/or soothing effect.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

FIG. 2A shows the results of mice that were observed in the open arms in an elevated plus maze (EPM-open) behavioral test. FIG. 2B shows the results of mice that were observed in the enclosed arms in an elevated plus maze (EPM-closed). FIG. 2C shows the results of the amount of time mice avoided the open center in an open field test (OFT) behavioral test. FIG. 2D shows the results of locomotor activity in an OFT behavioral test.

FIG. 4A shows the results of mice that were observed in the open arms in an elevated plus maze (EPM-open) behavioral test. FIG. 4B shows the results of mice that were observed in the enclosed arms in an elevated plus maze (EPM-closed). FIG. 4C shows the results of the amount of time mice avoided the open center in an open field test (OFT) behavioral test. FIG. 4D shows the results of locomotor activity in an OFT behavioral test.

DETAILED DESCRIPTION OF THE INVENTION

Figure 1:
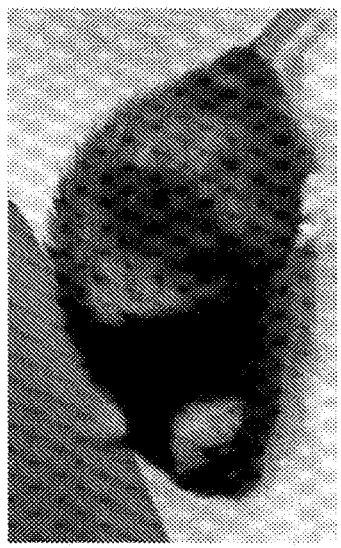
FIG. 1 shows that a chronically stressed mouse exhibited hair loss.

The invention provides, inter alia, methods of treating hair loss, methods of inducing hair growth, method of preventing hair loss, methods of delaying signs of aging skin, and methods of treating chronic stress by administering an effective amount of dihydromyricetin, or a derivative thereof. The invention also provides cosmetic products comprising at least 0.5 µM dihydromyricetin and/or purified dihydromyricetin, or a derivative thereof; and methods of making such cosmetic products.

The methods and compositions of the invention are based on the unexpected observation that applying dihydromyricetin, a natural flavonol extracted from plants, to the sites of hair loss induces new hair growth. Moreover, dihydromyricetin use does not produce the unpleasant side effects associated with other topical hair growth treatments, e.g., dryness, irritation, and allergic reaction.

A. Definitions

As used herein, a "dihydromyricetin compound" refers to dihydromyricetin, a dihydromyricetin derivative, or a salt thereof.

As used herein, "treating or preventing hair loss" refers to the ability to reduce, reverse, slow, or prevent symptoms of hair loss, including, but not limited to, alopecia, hair loss, thinning hair, uneven thickness of hair, and/or bald patches associated with, e.g., adrenergic alopecia, telogen effluvium, alopecia areata, traumatic alopecia, anagen effluvium, and hair loss associated with nutritional deficiencies, metabolic defects, marked weight loss, and chronic stress. Treating or preventing hair loss also includes promoting growth at the site(s) of the hair loss.

As used herein, to "induce hair growth" means to promote hair growth or re-growth or increase the amount of hair (such as new hair growth). For example, inducing hair growth encompasses promotion or stimulation of hair growth in general (e.g., to thicken naturally thin or thinning hair) or at the site(s) of baldness or hair loss.

As used herein, to "delaying or reversing signs of aging skin" means to defer, hinder, slow, retard, stabilize, and/or postpone development of symptoms of skin aging, including, but not limited to, the appearance of wrinkles, sagging skin, thinning skin, cornification, elastosis, the appearance of hyperpigmented spots (i.e., freckles, age spots, or "liver spots"), and/or dryness. This delay can be of varying lengths of time, depending on the condition of the skin and/or individual being treated.

As used herein, an "effective amount" refers to at least an amount effective, at dosages and for periods of time necessary, to achieve the desired result, e.g., induction of hair growth, prevention of hair loss, delaying or reversing signs of aging skin, or reduction in stress. An effective amount can be provided in one or more administrations.

As used herein, "alkyl" refers to a univalent group derived from a saturated hydrocarbon by removing one hydrogen atom. The saturated hydrocarbon may contain normal, secondary, or tertiary carbon atoms. These carbon atoms may be arranged in straight or branched chain, or in cyclic ring, or a combination thereof. For example, an alkyl group can have 1 to 20 carbon atoms (i.e., $C_1$-$C_{20}$ alkyl), 1 to 12 carbon atoms (i.e., $C_1$-$C_{12}$ alkyl), or 1 to 6 carbon atoms (i.e., $C_1$-$C_6$ alkyl). Examples of suitable alkyl groups include, but are not limited to, methyl (Me, —CH3), ethyl (Et, CH2CH3), 1-propyl (n-Pr, n-propyl, —CH2CH2CH3), 2-propyl Q-Pr, i-propyl, —CH(CHs)2), 1-butyl (n-Bu, n-butyl, —CH2CH2CH2CH3), 2-methyl-1-propyl Q-Bu, i-butyl, —C1hCH(CH$_3$)$_2$), 2butyl (s-Bu, s-butyl, —CH(CH$_3$)CH$_2$CH$_3$), 2-methyl-2-propyl (t-Bu, t-butyl, —C(CH$_S$)$_3$), 1-penty (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methy-1-butyl (—CH$_2$CH$_2$CH (CH$_3$)$_2$), 2-methyl-1-butyl (—CH$_2$CH(CH$_3$)CH$_2$CH$_3$), 1-hexyl (CH$_2$CH$_2$CH$_2$CH$_2$CH$_2$CH$_3$), 2-hexyl (—CH(CH$_3$) CH$_2$CH$_2$CH$_2$CH$_3$), 3-hexyl (CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (C(CH$_3$) (CH$_2$CH$_3$)$_2$), 2-methyl-3-pentyl (—CH(CH$_2$CH$_3$)CH (CH$_3$)$_2$), 2,3-dimethyl-2-butyl (C(CH$_3$)$_2$CH(CH$_3$)$_2$), 3,3-dimethyl-2-butyl (—CH(CH$_3$)C(CH$_3$)$_3$, and octyl (—(CH$_2$)$_7$CH$_3$).

As used herein, "alkylene" refers to a divalent group derived from an alkyl by removing one hydrogen atom. That is, "alkylene" can be a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 12 carbon atoms, or 1 to 6 carbon atoms. Typical alkylene radicals include, but are not limited to, methylene (—CH$_2$—), 1,1-ethyl (—CH(CH$_3$)—), 1,2-ethyl (—CH$_2$CH$_2$—), 1,1-propyl (—CH(CH$_2$CH$_3$)—), 1,2-propyl (—CH$_2$CH(CH$_3$)—), 1,3-propyl (—CH$_2$CH$_2$CH$_2$—), 1,4butyl (—CH$_2$CH$_2$CH$_2$CH$_2$—), and the like.

As used herein, "alkenyl" refers to a univalent group derived from a hydrocarbon by removing one hydrogen atom wherein the hydrocarbon contains at least one carbon-to-carbon double bond. For example, an alkenyl group can have 1 to 20 carbon atoms (i.e., C1-C20 alkenyl), 1 to 12 carbon atoms (i.e., C1-C12 alkenyl), or 1 to 6 carbon atoms (i.e., C1-C6 alkenyl). Typical alkenyl groups include, but are not limited to, ethenyl, prop-1-en-1-yl, prop-1-en-2-yl, prop-2-en-1-yl (allyl), cycloprop-1-en-1-yl; cycloprop-2-en-1-yl, but-1-en-1 yl, but-1-en-2-yl, 2-methyl-prop-1-en-1-yl, but- 2-en-1-yl, but-2-en-2-yl, buta-1,3-dien-1-yl, buta1,3-dien-2-yl, cyclobut-1-en-1-yl, cyclobut-1-en-3-yl, cyclobuta-1,3-dien-1-yl, and the like.

As used herein, "alkenylene" refers to a divalent group derived from an alkenyl by removing one hydrogen atom. That is, "alkenylene" can be an unsaturated, branched or straight chain or cyclic unsaturated hydrocarbon radical having two monovalent radical centers derived by the removal of two hydrogen atoms from the same or two different carbon atoms of a parent alkene.

As used herein, "alkoxyl" refers to a monovalent radical —OR wherein R is an alkyl or alkenyl.

As used herein, "halo" refers to a univalent group derived from a halogen element including, but not limited to, fluorine, chlorine, bromine, iodine, and astatine.

As used herein, "heteroalkyl" or "heteroalkenyl" refers to alkyl or alkenyl, respectively, in which one or more of the carbon atoms (and optionally any associated hydrogen atoms), are each, independently of one another, replaced with the same or different heteroatoms or heteroatomic groups. Similarly, "heteroalkylene" or "heteroalkenylene" refers to alkylene or alkenylene, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like, and combinations thereof. The heteroatoms or heteroatomic groups may be placed at any interior position of the alkyl or alkenyl. Typical heteroatomic groups which can be included in these groups include, but are not limited to, —O—, —S—, —O—O—, —S—S—, —O—S—, —N(R$^a$)$_2$—, =N—N=, —N=N—, —N=N—N(R$^a$)$_2$, —PR$^a$—, —P(O)$_2$—, —POR$^a$—, —O—P(O)$_2$—, —SO—, —SO$_2$—, —Sn(R$^a$)$_2$— and the like, where each R$^a$ is independently hydrogen, alkyl, substituted alkyl, aryl, substituted aryl, arylalkyl, substituted arylalkyl, cycloalkyl, substituted cycloalkyl, cyclohetero alkyl, substituted cycloheteroalkyl, heteroalkyl, substituted heteroalkyl, heteroaryl, substituted heteroaryl, heteroarylalkyl or substituted heteroarylalkyl, or a protecting group.

As used herein, "protecting group" refers to a grouping of atoms that when attached to a reactive functional group in a molecule masks, reduces or prevents reactivity of the functional group. Representative amino protecting groups include, but are not limited to, formyl, acetyl, trifluoroacetyl, benzyl, benzyloxycarbonyl ("CBZ"), tertbutoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarlbonyl ("FMOC"), nitro-veratryloxycarbonyl ("NVOC"), and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

As used here, "substituted," when used to modify a specified group or radical, refers to one or more hydrogen atoms of the specified group or radical are each, independently of one another, replaced with the same or different substituent(s). Substituent groups useful for substituting saturated carbon atoms in the specified group or radical include, but are not limited to, —R$^o$, halo, O$^n$, =O, —OR$^b$, —SR$^b$, —S$^n$, =S, —N(R$^d$)$_2$, =NR$^b$, =N—OR$^b$, trihalomethyl, —CF$_3$, —CN, —OCN, —SCN, NO, —NO$_2$, =N$_2$, —N$_3$, —S(O)$_2$R$^b$, —S(O)$_2$NR$^b$, —S(O)$_2$O$^n$, —S(O)$_2$OR$^b$, —OS(O)$_2$R$^b$, —OS(O)$_2$O$^n$, —OS(O)$_2$OR$^b$, —P(O)(O)$_2$, —P(O)(OR$^b$)(O$^n$), —P(O)(OR$^b$)(OR$^b$), —C(O)R$^b$, —C(S)R$^b$, —C(NR$^b$)R$^b$, C(O)O$^n$, —C(O)OR$^b$, —C(S)OR$^b$, —C(O)N(R$^d$)$_2$, —C(NR$^b$)N(R$^d$)$_2$, —OC(O)R$^b$, —OC(S)R$^b$, —OC(O)O$^n$, OC(O)OR$^b$, —OC(S)OR$^b$, —NR$^b$C(O)R$^b$, —NR$^b$C(S)R$^b$, —NR$^b$C(O)O$^n$, —NR$^b$C(O)OR$^b$, —NR$^b$C(S)OR$^b$, —NR$^b$C(O)N(R$^d$)$_2$, —NR$^b$C(NR$^b$)R$^b$, and —NR$^b$C(NR$^b$)N(R$^d$)$_2$, where R$^c$ is selected from alkyl, cycloalkyl, heteroalkyl, cycloheteroalkyl, aryl, arylalkyl, heteroaryl and heteroarylalkyl; each R$^b$ is independently hydrogen, a protecting group, or R$^o$; and each R$^d$ is independently R$^b$ or alternatively, the two R$^d$s may be taken together with the nitrogen atom to which they are bonded form a 4-, 5-, 6- or 7-membered cycloheteroalkyl which may optionally include from 1 to 4 of the same or different additional heteroatoms selected from O, N, and S. As specific examples, —N(R$^d$)$_2$ is meant to include —NH$_2$, —NH-alkyl, N-pyrrolidinyl, and N-morpholinyl. As another specific example, a substituted alkyl is meant to include -alkylene-O-alkyl, -alkylene-heteroaryl, -alkylene-cycloheteroalkyl, -alkyleneC(O)OR$^b$, -alkylene-C(O)N(R$^d$)$_2$, and —CH$_2$—CH$_2$—C(O)—CH$_3$. The one or more substituent groups, taken together with the atoms to which they are bonded, may form a cyclic ring including cycloalkyl and cycloheteroalkyl.

As used herein, the term "w/v-%" refers to the weight of a compound, such as dihydromyricetin, (in grams) for every 100 ml of a liquid product of the present disclosure containing such a compound, such as a hair product or other cosmetic products.

As used herein, the term "w/w-%" refers to the weight of a compound, such as dihydromyricetin, (in grams) for every gram of a product of the present disclosure containing such compound, such as a hair product or other cosmetic products.

An "individual" or a "subject" is a mammal, more preferably a human. Mammals also include, but are not limited to, farm animals, sport animals, pets (such as cats, dogs, horses), primates, mice and rats.

As used herein, the singular form "a", "an", and "the" includes plural references unless indicated otherwise.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X."

It is understood that aspects and embodiments of the invention described herein include "comprising," "consisting," and "consisting essentially of" aspects and embodiments.

B. Methods of Treating or Preventing Hair Loss, Promoting Hair Growth, Delaying the Signs of Aging Skin or Reversing the Signs of Aging Skin In one aspect, the invention provides methods for treating hair loss or inducing hair growth, and methods of preventing hair loss, that include applying an effective amount of a dihydromyricetin compound, such as dihydromyricetin, to the scalp of an individual. In certain embodiments of the methods, the dihydromyricetin compound is applied to the scalp of the individual through any known method, including but not limited to topically spreading, spraying, steaming, soaking, washing, etc. The methods can also be useful for other sites of hair loss or sites in which hair growth is desired, such as the chin (to promote, even out, or thicken beard growth), the sides of the face (to promote, even out, or thicken the growth of sideburns), between the nose and lip (to promote, even out, or thicken moustache growth), the chest, etc. An effective amount of the dihydromyricetin compound may be applied to these sites.

Another aspect of the invention provides methods for treating hair loss or inducing hair growth, and methods of preventing hair loss, that include applying an effective amount of a dihydromyricetin compound, such as dihydromyricetin, to the skin of an animal. In certain embodiments of the methods, the dihydromyricetin compound is applied to the skin of the animal through any known method, including but not limited to topically spreading, spraying, steaming, soaking, washing, etc. In certain embodiments, the animal is a pet animal, including without limitation, a dog, a cat, a horse, a rabbit, a hamster, a guinea pig, a hamster, etc.

In certain embodiments of the methods, the dihydromyricetin compound is provided in a hair product. In certain embodiments of the methods, the hair products that comprise the dihydromyricetin compound include, but are not limited to, e.g., shampoos, conditioners, masks, sprays or mists, gels, mousses, foams, serums, pastes, pomades, powders, oils, emulsions, creams, waxes, glazes, balms, tonics, lotions, ointments, polishes, lightening agents, straightening agents, relaxing agents, curling agents, or dyes. In certain embodiments of the methods, the dihydromyricetin compound in the hair product is at a concentration of about 0.01 µM to about 250 µM. For example, the dihydromyricetin compound in the hair product is at a concentration of about 0.01 µM, about 0.05 µM, about 0.1 τM, about 0.2 µM, about 0.3 µM, about 0.4 µM, 0.5 µM, about 0.6 µM, about 0.7 µM, about 0.8 µM, about 0.9 µM, about 1 µM, about 2 µM, about 3 µM, about 4 µM, about 5 µM, about 6 µM, about 7 µM, about 8 µM, about 9 µM, about 10 µM, about 25 µM, about 50 µM, about 100 µM, about 150 µM, about 200 µM, or about 250 µM, including any range in between these values.

In certain embodiments of the methods, the dihydromyricetin compound in the hair product is at a concentration of at least about 5% (w/v-%) or at least about 5% (w/w-%) to at least about 25% (w/v-%) or at least about 25% (w/w-%). For example, the dihydromyricetin compound in the hair product is at a concentration of at least about 5% (w/v-%) or at least about 5% (w/w-%), at least about 6% (w/v-%) or at least about 6% (w/w-%), at least about 7% (w/v-%) or at least about 7% (w/w-%), at least about 8% (w/v-%) or at least about 8% (w/w-%), at least about 9% (w/v-%) or at least about 9% (w/w-%), at least about 10% (w/v-%) or at least about 10% (w/w-%), at least about 11% (w/v-%) or at least about 11% (w/w-%), at least about 12% (w/v-%) or at least about 12% (w/w-%), at least about 13% (w/v-%) or at least about 13% (w/w-%), at least about 14% (w/v-%) or at least about 14% (w/w-%), at least about 15% (w/v-%) or at least about 15% (w/w-%), at least about 16% (w/v-%) or at least about 16% (w/w-%), at least about 17% (w/v-%) or at least about 17% (w/w-%), at least about 18% (w/v-%) or at least about 18% (w/w-%), at least about 19% (w/v-%) or at least about 19% (w/w-%), at least about 20% (w/v-%) or at least about 20% (w/w-%), at least about 21% (w/v-%) or at least about 21% (w/w-%), at least about 22% (w/v-%) or at least about 22% (w/w-%), at least about 23% (w/v-%) or at least about 23% (w/w-%), at least about 24% (w/v-%) or at least about 24% (w/w-%), or at least about 25% (w/v-%) or at least about 25% (w/w-%), including any range in between these values.

In certain embodiments, the compound in a relatively higher concentration is applied to treat hair loss or induce hair growth, and the compound in a relatively lower concentration is applied to maintain the amount of hair. In some embodiments, "preventing hair loss" includes maintaining hair growth and/or the amount of hair resulting from hair growth (such as induced hair growth). Also provided herein is a method of maintaining the amount of hair comprising applying an effective amount of a dihydromyricetin compound described herein to scalp of an individual or other sites.

In certain embodiments of the methods, the individual suffers from chronic stress, alopecia, thinning hair, bald patches, and/or baldness. In certain embodiments, alopecia, thinning hair, hair loss, bald patches, and/or baldness is associated with chronic stress and/or anxiety. In certain embodiments of the methods, the individual has telogen effluvium (TE) or alopecia areata.

In another aspect, the invention provides methods for delaying or reversing signs of aging skin comprising applying an effective amount of a dihydromyricetin compound, such as dihydromyricetin, to the skin of an individual, including, but not limited to, e.g., to the face, the neck, the decolletage, the hands, the arms, the shoulders, the legs, etc. In certain embodiments, the dihydromyricetin compound delays or reverses the appearance of wrinkles and folds, scaliness, flakiness, roughness and/or other forms of uneven skin texture, sagging skin, thinning skin, cornification, elastosis or loss of skin elasticity, discoloration (such as under eye circles), blotching, sallowness, hyperpigmented skin regions (such as age spots, "liver spots", and/or freckles), keratoses, solar purpuras, hyperkeratinization, telangiectasia (i.e., "spider vessels"), and/or dryness.

In certain embodiments of the methods, the dihydromyricetin compound is provided in a skin product. In certain embodiments of the methods, the skin product containing the dihydromyricetin compound is a lotion, a moisturizer, a facial polisher, a facial cleanser, a sunscreen, a skin patch, a scrub or exfoliating product, an astringent, a toner, a mask, a peel, a gel, a cream, a balm, a wax, an oil, a salve, a makeup remover, an insect repellent, a soap, a makeup product (e.g., a foundation, a primer, a concealer or color corrector, a blusher or rouge, a lipstick, a lip gloss, a lip balm, a bronzer, a powder, a setting spray, etc.), a mist or spray, an ointment, a liniment, a topical analgesic, a topical antihistamine, or an emulsion. In certain embodiments of the methods, the dihydromyricetin compound in the skin product is at a concentration of about 0.01 µM to about 250 µM. For example, the dihydromyricetin compound in the skin product is at a concentration of about 0.01 µM, about 0.05 µM, about 0.1 µM, about 0.2 µM, about 0.3 µM, about 0.4 µM, 0.5 µM, about 0.6 µM, about 0.7 µM, about 0.8 µM, about 0.9 µM, about 1 µM, about 2 µM, about 3 µM, about 4 µM, about 5 µM, about 6 µM, about 7 µM, about 8 µM, about 9 µM, about 10 µM, about 25 µM, about 50 µM, about 100 µM, about 150 µM, about 200 µM, or about 250 µM, including any range in between these values. In certain embodiments of the methods, the dihydromyricetin compound in the skin product is at a concentration of at least about 5% (w/v-%) or at least about 5% (w/w-%) to at least about 25% (w/v-%) or at least about 25% (w/w-%). For example, the dihydromyricetin compound in the skin product is at a concentration of about at least 5% (w/v-%) or at least about 5% (w/w-%), at least about 6% (w/v-%) or at least about 6% (w/w-%), at least about 7% (w/v-%) or at least about 7% (w/w-%), at least about 8% (w/v-%) or at least about 8% (w/w-%), at least about 9% (w/v-%) or at least about 9% (w/w-%), at least about 10% (w/v-%) or at least about 10% (w/w-%), at least about 11% (w/v-%) or at least about 11% (w/w-%), at least about 12% (w/v-%) or at least about 12% (w/w-%), at least about 13% (w/v-%) or at least about 13% (w/w-%), at least about 14% (w/v-%) or at least about 14% (w/w-%), at least about 15% (w/v-%) or at least about 15% (w/w-%), at least about 16% (w/v-%) or at least about 16% (w/w-%), at least about 17% (w/v-%) or at least about 17% (w/w-%), at least about 18% (w/v-%) or at least about 18% (w/w-%), at least about 19% (w/v-%) or at least about 19% (w/w-%), at least about 20% (w/v-%) or at least about 20% (w/w-%), at least about 21% (w/v-%) or at least about 21% (w/w-%), at least about 22% (w/v-%) or at least about 22% (w/w-%), at least about 23% (w/v-%) or at least about 23% (w/w-%), at least about 24% (w/v-%) or at least about 24% (w/w-%), or at least about 25% (w/v-%) or at least about 25% (w/w-%), including any range in between these values.

In certain embodiments of the methods, the individual suffers from chronic stress. In certain embodiments of the methods, the individual has a skin rash, has dehydrated skin, or exhibits physical, psychological, or emotional symptoms of chronic stress. In certain embodiments, the skin rash and/or skin dehydration is associated with chronic stress and/or anxiety.

In another aspect, the invention provides methods of treating the psychological, physical, or emotional changes associated with chronic stress comprising applying an effective amount of a dihydromyricetin compound, such as dihydromyricetin, to the individual's skin and/or scalp. In certain embodiments of the methods, the dihydromyricetin compound is provided in a hair product or a skin product described in detail elsewhere herein. In certain embodiments of the methods, the dihydromyricetin compound in the hair product or the skin product is at a concentration of about 0.01 µM to about 250 µM. For example, the dihydromyricetin compound in the hair or skin product is at a concentration of about 0.01 µM, about 0.05 µM, about 0.1 µM, about 0.2 µM, about 0.3 µM, about 0.4 µM, 0.5 µM, about 0.6 µM, about 0.7 µM, about 0.8 µM, about 0.9 µM, about 1 µM, about 2 µM, about 3 µM, about 4 µM, about 5 µM, about 6 µM, about 7 µM, about 8 µM, about 9 µM, about 10 µM, about 25 µM, about 50 µM, about 100 µM, about 150 µM, about 200 µM, or about 250 µM, including any range in between these values. In certain embodiments of the methods, the dihydromyricetin compound in the hair product or the skin product is at a concentration of at least about 5% (w/v-%) or at least about 5% (w/w-%) to at least about 25% (w/v-%) or at least about 25% (w/w-%). For example, the dihydromyricetin compound in the hair or skin product is at a concentration of about at least about 5% (w/v-%) or at least about 5% (w/w-%), at least about 6% (w/v-%) or at least about 6% (w/w-%), at least about 7% (w/v-%) or at least about 7% (w/w-%), at least about 8% (w/v-%) or at least about 8% (w/w-%), at least about 9% (w/v-%) or at least about 9% (w/w-%), at least about 10% (w/v-%) or at least about 10% (w/w-%), at least about 11% (w/v-%) or at least about 11% (w/w-%), at least about 12% (w/v-%) or at least about 12% (w/w-%), at least about 13% (w/v-%) or at least about 13% (w/w-%), at least about 14% (w/v-%) or at least about 14% (w/w-%), at least about 15% (w/v-%) or at least about 15% (w/w-%), at least about 16% (w/v-%) or at least about 16% (w/w-%), at least about 17% (w/v-%) or at least about 17% (w/w-%), at least about 18% (w/v-%) or at least about 18% (w/w-%), at least about 19% (w/v-%) or at least about 19% (w/w-%), at least about 20% (w/v-%) or at least about 20% (w/w-%), at least about 21% (w/v-%) or at least about 21% (w/w-%), at least about 22% (w/v-%) or at least about 22% (w/w-%), at least about 23% (w/v-%) or at least about 23% (w/w-%), at least about 24% (w/v-%) or at least about 24% (w/w-%), or at least about 25% (w/v-%) or at least about 25% (w/w-%), including any range in between these values.

In certain embodiments of the methods, the individual has alopecia, thinning hair, and/or baldness. In certain embodiments of the methods, the individual has telogen effluvium (TE) or alopecia areata. In certain embodiments of the methods, the individual exhibits signs of aging skin, e.g., the symptoms of aging skin described elsewhere herein. In certain embodiments, the individual may exhibit the physical, psychological, and/or emotional symptoms of chronic stress, including, but not limited to, e.g., gingivitis, upset stomach or other digestive discomfort, dizziness and/or backache, insomnia, chest discomfort, moodiness, anxious, nervousness, aggression, intense mood swings, rash, poor concentration, heightened confusion in stressful situations, inability to complete tasks, unstable blood pressure, hemorrhoids, varicose veins, panic attacks, and suicidal thoughts.

In certain embodiments of any methods described above, the dihydromyricetin compound is purified from whole plant or plant tissues. In certain embodiments, the dihydromyricetin compound is purified from *Hovenia dulcis*, *Leptarrhena pyrolifolia*, *Pinus contorta*, *Ampelopsis grossedentata*, *Glochidion sumatranum*, *Rhododendron ferrugineum*, *Erica arborea*, *Salix hulteni*, *Manilkara zapota*, *Catharanthus roseus*, *Myrica rubra*, or *Xanthoceras sorbifolia*. In certain embodiments of any methods described above, the dihydromyricetin compound is synthesized using methods known in the art, and may be further purified. In certain embodiments, the dihydromyricetin compound is chemically synthesized. In certain embodiments, the dihydromyricetin is purchased from a distributor.

Dihydromyricetin Compounds

As used herein, dihydromyricetin compounds include, without limitation, flavonoids having formula (I):

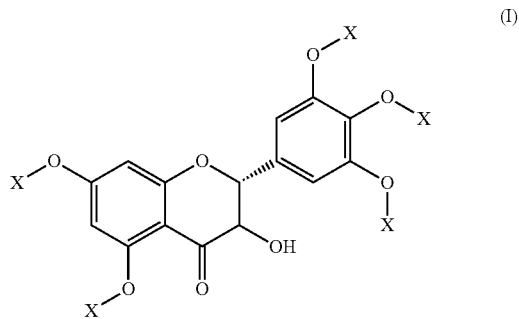

where each X is independently selected from hydrogen, alkyl, substituted alkyl, alkenyl, substituted alkenyl, halo, alkoxyl, heteroalkyl, substituted heteroalkyl, heteroalkenyl, or substituted heteroalkenyl.

In certain embodiments of formula (I), X is independently selected from —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —CH$_2$C(CH$_3$)$_2$CH$_3$, —C(CH$_3$)$_2$CH$_2$CH$_3$, —CH$_2$CH$_2$CH(CH$_3$)$_2$, —CH$_2$CH$_2$CH$_2$CH$_2$CH$_3$, —CH$_2$C(CH$_3$)$_2$CH$_2$CH$_3$, —CH$_2$CH$_2$C(CH$_3$)$_2$CH$_3$, —CH$_2$CH$_2$CH$_2$CH(CH$_3$)$_2$, —CH$_2$CH(CH$_2$CH$_3$)CH$_2$CH$_3$, —CH$_2$CH$_2$OCH$_3$, —CH$_2$CH$_2$CH$_2$OCH$_3$, —CH$_2$CH$_2$CH$_2$OCH$_2$CH$_3$, and —CH$_2$CH$_2$CH$_2$CH$_2$OCH$_2$CH$_3$.

In certain embodiments, the dihydromyricetin compound is of formula (II):

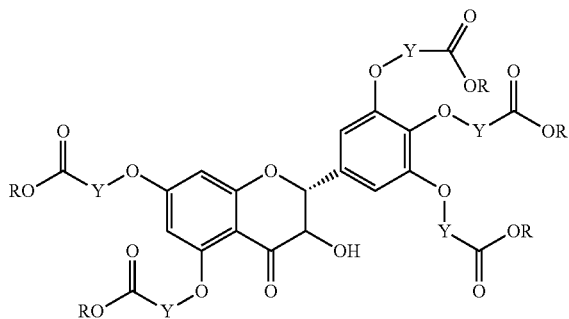

(II)

where each Y is independently selected from is C$_{1-12}$ alkylene or C$_{1-12}$ alkenylene; and where each R is independently C$_1$ 12 alkyl.

In certain embodiments, the dihydromyricetin compound is of formula (III):

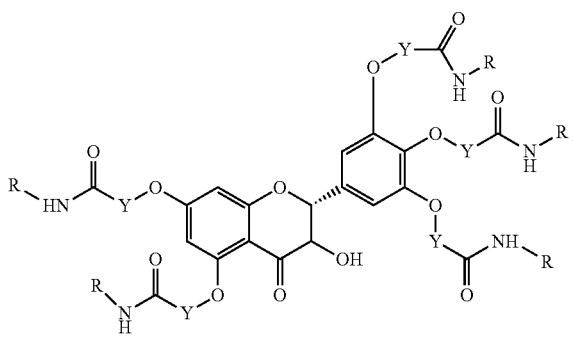

(III)

where each Y is independently selected from is C$_{1-12}$ alkylene or C$_{1-12}$ alkenylene; and where each R is independently C$_{1-12}$ alkyl.

In certain embodiments, the dihydromyricetin compound having formula (I) has hydrogen at position X. In such embodiments where X is a hydrogen, the dihydromyricetin compound is dihydromyricetin.

Dihydromyricetin compounds, such as dihydromyricetin, may be in the form of a salt which is produced by mixing dihydromyricetin with a base or the like. The present disclosure provides for such salts of dihydromyricetin compounds.

The terms "salts" as used herein refer to cosmetically acceptable or pharmaceutically acceptable base-addition salt forms of dihydromyricetin compounds, such as dihydromyricetin. Cosmetically acceptable salts are those which are acceptable for topical applications and pharmaceutically acceptable salts are those which are acceptable for topical pharmaceutical use, said salts being non-toxic. Said base-addition salt forms in particular are alkali metal, e.g. sodium or potassium, or ammonium, or substituted ammonium salt forms, or salts with amino acids such as, for example, arginine, lysine and the like. Substituted ammonium as used herein refers to any non-toxic substituted ammonium ion known or used in the art as a salt former and comprises mono-, di-, and in particular tri- or quaternary substituted ammonium salts, including mono- or polycyclic systems. Substituents on ammonium for example are alkyl, cycloalkyl, alkenyl, substituted alkyl such as hydroxyalkyl, alkyloxyalkyl, (cycloalkyl)alkyl, arylalkyl such as benzyl, and the like.

As used herein, dihydromyricetin [(2R,3R)-3,5,7-trihydroxy-2-(3,4,5-trihydroxyphenyl)-2,3-dihydrochromen-4-one], also known as ampelopsin, is a flavonoid compound having the structure depicted below:

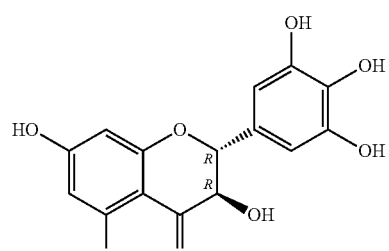

Dihydromyricetin (DHM)
C$_{15}$H$_{12}$O$_8$ MW: 320.25

Dihydromyricetin has been found in a variety of plants, including, e.g., *Hovenia dulcis* (Ding et al. (1997) "Study on flavonoids in seeds of *Hovenia dulcis*." Yao Xue Xue Bao. 32: 600-2), *Leptarrhena pyrolifolia* and *Pinus contorta* (Stafford, et al. (1985) "Flavan-3-ol Biosynthesis: The Conversion of (+)-Dihydromyricetin to Its Flavan-3,4-Diol (Leucodelphinidin) and to (+)-Gallocatechin by Reductases Extracted from Tissue Cultures of *Ginkgo biloba* and *Pseudotsuga menziesii*." Plant Physiol. 78: 791-4), *Ampelopsis grossedentata* (Du et al. (2002) "Purification of (+)-dihydromyricetin from leaves extract of *Ampelopsis grossedentata* using high-speed countercurrent chromatograph with scale-up triple columns." J. Chromatogr. A. 973: 217-20), *Glochidion sumatranum* (Yin et al. (2010) "New galloylated flavanonols from the Australian plant *Glochidion sumatranum*." Planta Med. 76: 1877-1881), *Rhododendron ferrugineum* (Louis et al. (2010) "Phytochemical characterization of *Rhododendron ferrugineum* and in vitro assessment of an aqueous extract on cell toxicity." Planta Med. 76: 1550-7), *Erica arborea* (Nazimiyeh et al. (2008) "Antioxidant phenolic compounds from the leaves of *Erica Arborea* (Ericaceae)." Nat Prod Res. 22: 1385-92), *Salix hulteni* (Jeon et al. (2008) "Cytotoxic constituents from the bark of *Salix hulteni*." Arch Pharm Res. 31: 978-982), *Manilkara zapota* (Ma et al. (2003) "Bioactive novel polyphenols from the fruit of *Manilkara zapota* (Sapodilla)." J Nat Prod. 66: 983-986), *Catharanthus roseus* (Cacace et al. (2003) "A flavonol O-methyltransderase from *Catharanthus roseus* performing two sequential methylations." Phytochemistry. 62: 127-137) and *Xanthoceras sorbifolia* (Ni et al. 2009) "Studies on the chemical constituents of *Xanthoceras sorbifolia*." Zhong Yao Cai. 32: 702-704). Other natural source of dihydromyricetin includes *Myrica Rubra* (also called Chinese bayberry, Japanese bayberry, red bayberry, yumberry, waxberry, or Chinese strawberry).

Dihydromyricetin can be extracted from these and other plants using techniques well known in the art. For example, dihydromyricetin extraction and purification methods are described in Yoo et al. (2006) "Recovery and pre-purification of (+)-dihydromyricetin from *Hovenia dulcis*." *Process Biochem* 41: 567-570; Li et al. (2008) "Comparison of refluxing, ultrasonic- and microwave-assisted extraction of dihydromyricetin from *Ampelopsis grossedentata*." *J AOAC Int.* 91: 1278-83; Du et al. (2002) "Purification of (+)-dihydromyricetin from leaves extract of *Ampelopsis grossedentata* using high-speed countercurrent chromatograph with scale-up triple columns." *J Chromatog A* 973: 217-220; and others. Extraction methods described in Example 1 may also be used, The following method may also be used for extracting and purifying dihydromyricetin from a whole plant or plant tissues:

Biomass Extraction:

The plant biomass is added to hot water at a ratio of 1:10 (w/v). The extraction begins with the biomass mixed with hot water and is stirred at 100° C. for 6 h. The mixture is filtered through filter paper in a Buchner funnel under vacuum. These procedures are repeated at least three times. Each water extract is collected, pooled, and concentrated at 40° C. under reduced pressure to decrease the volume of the water extract to 20% of its original.

Liquid-Liquid Extraction:

The concentrated water extract is added to organic solvents (ethyl ether, chloroform, ethyl acetate, methyl-t-butyl ether, butanol) at a volume ratio of 4:1 for liquid-liquid extraction, and this is extracted at room temperature for 30 min. The extraction is repeated at least three times, and the crude extracts were pooled and dried at room temperature under a reduced pressure.

Adsorbent Treatment of the Crude Extract:

The dried crude extract from the liquid-liquid extraction is dissolved in methanol at a ratio of 20 (v/w) of methanol-to-dried crude extract, and several synthetic adsorbents were added and tested individually, including the active clays P-1 and P-1G (Mizukalife Chemical Co., Japan), the activated carbons CA-1 and SX-PLUS (Norit, The Netherlands), and sylopute (Fuji Silysia Chemical Ltd., Japan) at a ratio of 0.5 (w/w) of synthetic adsorbent to dried crude extract. The mixtures are stirred at room temperature for 30 min and filtered to obtain the filtration solution. The adsorbent cake thus obtained, is washed several times with ethyl ether/methanol (1:1, v/v) and the washings are combined with the filtration solution. The solution is dried at 40° C. under a reduced pressure for the chromatography.

Silica Gel Low-Pressure Chromatography:

The dried crude extract obtained after the adsorbent treatment is dissolved in methanol at a ratio of 10 (v/w) of methanol-to-dried crude extract and then filtered through diatomaceous earth (Fuji Silysia Chemical Ltd., Japan). The filter aid is washed five times with methanol, and the washings are combined. The resulting solution is applied to a 25 mm×400 mm column packed with silica gel 60N (Merck, Germany), which is equilibrated with ethyl ether. The column is eluted using an isocratic method with the same solvent. The fractions containing (+)-dihydromyricetin are collected and dried by rotary evaporation.

The purity of dihydromyricetin extracted is assayed using methods known in the art. For example, HPLC may be used to test the purity of dihydromyricetin extracts. An HPLC system (Waters, Milford, USA) may be used for the analytical characterization of the intermediate and final products. Purified dihydromyricetin extract may be analyzed using a C18 column (4.6 mm×250 mm, 5 mm, Shiseido, Japan). The column is eluted with a water/acetonitrile gradient from 90:10 (v/v) to 30:70 (v/v) at a flow rate of 1.0 mL/min. The injection volume is 20 ml, and the effluent is monitored at 254 nm with a UV detector. The dried residue is resolved in water and used for the quantitative analysis of (+)-dihydromyricetin. Authentic (+)-dihydromyricetin (purity: 98%) may be purchased from Biopurify Phytochemicals Ltd (China) and used as a standard.

Dihydromyricetin is also commercially available from a variety of manufacturers, including, e.g., Selleckchem, 2626 South Loop West, Suite 225, Houston, Tex. 77054, USA; Shaanxi Huisheng Medicament Technology Co., Ltd., No. 78 Ping An Road, Yanglin High & New Technology Area, Shaanxi, China; Hunan 3W Botanical Extract Inc., C401, BLDG 1, International Enterprise Center, No. 188 Middle Huanbao Rd., Hunan, China; Phyto Nutraceutical Inc., Tai-Jia R, Wangcheng Xian, Changsha City, Hunan, China; and others.

Dihydromyricetin compounds can be produced by chemically altering dihydromyricetin using methods well known to those of skill in the art. Alternatively, dihydromyricetin compounds can be chemically synthesized using methods well known to those of skill in the art.

C. Cosmetic Products Comprising Dihydromyricetin Compounds

In another aspect, the invention provides cosmetic products comprising a dihydromyricetin compound, such as dihydromyricetin. In some embodiments, the dihydromyricetin compound in the cosmetic product is at a concentration of about 0.01 μM to about 250 μM. In certain embodiments, a purified dihydromyricetin compound, such as purified dihydromyricetin, is added to the cosmetic product or a material from which the cosmetic product is made. In certain embodiments, the cosmetic product can be a hair product or a skin product, e.g., including, but not limited to a hair or skin product described elsewhere herein.

In certain embodiments, the purified dihydromyricetin compound has been added directly to the cosmetic product or to a material from which the cosmetic product is made. A material used to make a cosmetic product can comprise, e.g., a single ingredient or multiple ingredients, to which further ingredients are added following the addition of the dihydromyricetin compound. The material can be a subset of ingredients used to make the cosmetic product. The material can be treated (i.e., heated, filtered, evaporated, mixed, liquefied, aerosolized, etc.) before or after the addition of the dihydromyricetin compound.

In certain embodiments, the dihydromyricetin compound is purified from whole plant or plant tissues (such as fruits). In certain embodiments, the dihydromyricetin compound is purified from *Hovenia dulcis, Leptarrhena pyrolifolia, Pinus contorta, Ampelopsis grossedentata, Glochidion sumatranum, Rhododendron ferrugineum, Erica arborea, Salix hulteni, Manilkara zapota, Catharanthus roseus, Xantheoceras sorbifolia*, or *Myrica rubra*. In certain embodiments, the dihydromyricetin compound is chemically synthesized. In certain embodiments, the dihydromyricetin compound is purchased from a distributor.

In certain embodiments, the dihydromyricetin compound that has been added to the cosmetic product or to a material from which the cosmetic product is made is at least about 80% pure, at least about 85% pure, at least about 90% pure, at least about 91% pure, at least about 92% pure, at least about 93% pure, at least about 94% pure, or at least about 95% pure. In certain embodiments, the dihydromyricetin compound that has been added to the cosmetic product or to a material from which the cosmetic product is made is more than 95% pure, e.g., at least about 96% pure, at least about 97% pure, at least about 98% pure, at least about 99% pure, or about 99% pure.

In certain embodiments, the dihydromyricetin compound in the cosmetic product (e.g., a hair product or skin product) is at a concentration of about 0.01 µM to about 250 µM. For example, the dihydromyricetin compound in the cosmetic product is at a concentration of about 0.01 µM, about 0.05 µM, about 0.1 µM, about 0.2 µM, about 0.3 µM, about 0.4 µM, 0.5 µM, about 0.6 µM, about 0.7 µM, about 0.8 µM, about 0.9 µM, about 1 µM, about 2 µM, about 3 µM, about 4 µM, about 5 µM, about 6 µM, about 7 µM, about 8 µM, about 9 µM, about 10 µM, about 25 µM, about 50 µM, about 100 µM, about 150 µM, about 200 µM, or about 250 µM, including any range in between these values. In certain embodiments, the dihydromyricetin compound in the cosmetic product (e.g., a hair product or skin product) is at a concentration of about at least about 5% (w/v-%) or at least about 5% (w/w-%), at least about 6% (w/v-%) or at least about 6% (w/w-%), at least about 7% (w/v-%) or at least about 7% (w/w-%), at least about 8% (w/v-%) or at least about 8% (w/w-%), at least about 9% (w/v-%) or at least about 9% (w/w-%), at least about 10% (w/v-%) or at least about 10% (w/w-%), at least about 11% (w/v-%) or at least about 11% (w/w-%), at least about 12% (w/v-%) or at least about 12% (w/w-%), at least about 13% (w/v-%) or at least about 13% (w/w-%), at least about 14% (w/v-%) or at least about 14% (w/w-%), at least about 15% (w/v-%) or at least about 15% (w/w-%), at least about 16% (w/v-%) or at least about 16% (w/w-%), at least about 17% (w/v-%) or at least about 17% (w/w-%), at least about 18% (w/v-%) or at least about 18% (w/w-%), at least about 19% (w/v-%) or at least about 19% (w/w-%), at least about 20% (w/v-%) or at least about 20% (w/w-%), at least about 21% (w/v-%) or at least about 21% (w/w-%), at least about 22% (w/v-%) or at least about 22% (w/w-%), at least about 23% (w/v-%) or at least about 23% (w/w-%), at least about 24% (w/v-%) or at least about 24% (w/w-%), or at least about 25% (w/v-%) or at least about 25% (w/w-%), including any range in between these values.

In certain embodiments, the cosmetic products are hair products, including, but not limited to, e.g., shampoos, conditioners, masks, sprays or mists, gels, mousses, foams, serums, pastes, pomades, powders, oils, emulsions, creams, waxes, glazes, balms, tonics, lotions, ointments, polishes, lightening agents, straightening agents, relaxing agents, curling agents, or dyes. In certain embodiments, the cosmetic products are skin products, including, but not limited to, e.g., lotions, moisturizers, facial polishers, facial cleaners or cleansers, sunscreens, skin patches, scrubs or exfoliating products, astringents, toners, masks, peels, gels, creams, balms, waxes, oils, salves, makeup removers, insect repellents, soaps, makeup products (e.g., foundations, concealers or color correctors, blushers or rouges, lipsticks, lip glosses, lip balms, bronzers, setting sprays, powders, etc.), a mist, a spray, an ointment, a liniment, a topical analgesic, a topical antihistamine, or an emulsion.

The invention also provide methods of applying a cosmetic product described herein to a skin or hair area of an individual to treat hair loss, promote hair growth, delay or reverse signs of aging skin, or treating chronic stress or anxiety.

D. Methods of Making Cosmetic Products Comprising Dihydromyricetin Compounds

In yet another aspect, the invention provides methods of making a cosmetic product (e.g., a hair product or a skin product) comprising adding a dihydromyricetin compound, such as dihydromyricetin, to the cosmetic product or to a material from which the cosmetic product is made. In some embodiments, a purified dihydromyricetin compound, such as purified dihydromyricetin, is used in the methods, for example with purity between at least about 80% pure and at least about 99% pure, or greater than about 99% pure, as described herein. In certain embodiments, the methods are used to make a hair product or a skin product, as described elsewhere herein. In certain embodiments, the final concentration of the dihydromyricetin compound in the cosmetic product is between about 0.01 µM and about 250 µM.

In certain embodiments, the purified dihydromyricetin compound has been added directly to the cosmetic product or to a material from which the cosmetic product is made. A material used to make a cosmetic product can comprise, e.g., a single ingredient or multiple ingredients, to which further ingredients are added following the addition of the dihydromyricetin compound. The material can be a subset of ingredients used to make the cosmetic product. The material can be treated (i.e., heated, filtered, evaporated, mixed, liquefied, aerosolized, etc.) before or after the addition of the dihydromyricetin compound.

In certain embodiments, the dihydromyricetin compound is purified from whole plant or plant tissues. In certain embodiments, the dihydromyricetin compound is purified from *Hovenia dulcis*, *Leptarrhena pyrolifolia*, *Pinus contorta*, *Ampelopsis grossedentata*, *Glochidion sumatranum*, *Rhododendron ferrugineum*, *Erica arborea*, *Salix hulteni*, *Manilkara zapota*, *Catharanthus roseus*, *Myrica rubra*, or *Xanthoceras sorbifolia*. In certain embodiments, the dihydromyricetin compound is chemically synthesized. In certain embodiments, the dihydromyricetin compound is purchased from a distributor.

In certain embodiments, the dihydromyricetin compound that has been added to the cosmetic product or to a material from which the cosmetic product is made is at least about 80% pure, at least about 85% pure, at least about 90% pure, at least about 91% pure, at least about 92% pure, at least about 93% pure, at least about 94% pure, or at least about 95% pure. In certain embodiments, the dihydromyricetin compound that has been added to the cosmetic product or to a material from which the cosmetic product is made is more than 95% pure, e.g., at least about 96% pure, at least about 97% pure, at least about 98% pure, at least about 99% pure, or about 99% pure.

In certain embodiments of the methods, the dihydromyricetin compound in the cosmetic product (e.g., a hair product or skin product) is at a final concentration of about 0.01 µM, about 0.05 µM, about 0.1 µM, about 0.2 µM, about 0.3 µM, about 0.4 µM, 0.5 µM, about 0.6 µM, about 0.7 µM, about 0.8 µM, about 0.9 µM, about 1 µM, about 2 µM, about 3 µM, about 4 µM, about 5 µM, about 6 µM, about 7 µM, about 8 µM, about 9 µM, about 10 µM, about 25 µM, about 50 µM, about 100 µM, about 150 µM, about 200 µM, or about 250 µM, including any range in between these values. In certain embodiments of the methods, the dihydromyricetin compound in the cosmetic product (e.g., a hair product or skin product) is at a concentration of about at least about 5% (w/v-%) or at least about 5% (w/w-%), at least about 6% (w/v-%) or at least about 6% (w/w-%), at least about 7% (w/v-%) or at least about 7% (w/w-%), at least about 8% (w/v-%) or at least about 8% (w/w-%), at least about 9% (w/v-%) or at least about 9% (w/w-%), at least about 10% (w/v-%) or at least about 10% (w/w-%), at least about 11% (w/v-%) or at least about 11% (w/w-%), at least about 12% (w/v-%) or at least about 12% (w/w-%), at least about 13%

(w/v-%) or at least about 13% (w/w-%), at least about 14% (w/v-%) or at least about 14% (w/w-%), at least about 15% (w/v-%) or at least about 15% (w/w-%), at least about 16% (w/v-%) or at least about 16% (w/w-%), at least about 17% (w/v-%) or at least about 17% (w/w-%), at least about 18% (w/v-%) or at least about 18% (w/w-%), at least about 19% (w/v-%) or at least about 19% (w/w-%), at least about 20% (w/v-%) or at least about 20% (w/w-%), at least about 21% (w/v-%) or at least about 21% (w/w-%), at least about 22% (w/v-%) or at least about 22% (w/w-%), at least about 23% (w/v-%) or at least about 23% (w/w-%), at least about 24% (w/v-%) or at least about 24% (w/w-%), or at least about 25% (w/v-%) or at least about 25% (w/w-%), including any range in between these values.

In certain embodiments, the cosmetic products are hair products, including, but not limited to, e.g., shampoos, conditioners, masks, sprays or mists, gels, mousses, foams, serums, pastes, pomades, powders, oils, emulsions, creams, waxes, glazes, balms, tonics, lotions, ointments, polishes, lightening agents, straightening agents, relaxing agents, curling agents, or dyes. In certain embodiments, the cosmetic products are skin products, including, but not limited to, e.g., lotions, moisturizers, facial polishers, facial cleaners or cleansers, sunscreens, skin patches, scrubs or exfoliating products, astringents, toners, masks (e.g., facial masks), pads peels, gels, creams, balms, waxes, oils, salves, makeup removers, insect repellents, soaps, bath salts, makeup products (e.g., foundations, concealers or color correctors, blushers or rouges, lipsticks, lip glosses, lip balms, bronzers, setting sprays, powders, etc.), a mist, a spray, an ointment, a liniment, a topical analgesic, a topical antihistamine, an emulsion, or a facial treatment kits.

E. Kits and Articles of Manufacture

The invention also provides kits and articles of manufacture comprising a cosmetic product of the invention packaged in a container with a label indicating that the product is useful for promoting hair growth, reversing hair loss (or balding), promoting natural hair regrowth, increasing the thickness of thin (or thinning) hair, or preventing hair loss (or balding). The invention also provides kits and articles of manufacture comprising a cosmetic product of the invention packaged in a container with a label indicating that the product is useful for delaying skin aging or reversing the signs of skin aging. In certain embodiments, the label may further indicate that the product has a stress reducing, calming, and/or soothing effect. In certain embodiments, the label indicates the ingredients of the cosmetic product include a dihydromyricetin compound, such as dihydromyricetin.

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Use of Dihydromyricetin (DHM) in the Treatment of Stress-Induced Hair Loss Dihydromyricetin (DHM) was extracted and purified from *Hovenia dulcis*. The extraction process involved the following steps. *Hovenia dulcis* plants (such as fruits) were extracted with 70% ethanol in 10-fold volume of the plant tissues at 80-85° C. using soxhlet extraction (apparatus). The extraction was performed twice. The first extraction was 2 hours, and the second extraction was 1.5 hours. The extract was cooled down to room temperature and filtered. The filtrate was concentrated to crystalize the compounds in the reactor and then centrifuged to isolate precipitates. The precipitates were further extracted with 8-fold volume of 80% ethanol for 1 hour at 80-85° C. using soxhlet extraction (apparatus). The extract was cooled down to room temperature and filtered. The filtrate was concentrated to recrystallize the compounds in the reactor. The filtrate was centrifuged to isolate precipitates, and the precipitates were then dried at 75-80° C. under ordinary atmospheric pressure. The dried material was ground into powder which is the final product (BluCetin™). The product BluCetin™ contains ≥98% DHM as tested by HPLC.

To determine whether topical application of DHM is toxic or causes allergic reaction, Vaseline mixed with 1 g DHM was applied to the shaved skin of c57BL/6J mice for six weeks. The animals did not exhibit rash, redness, or other responses associated with an allergic reaction. In addition, the animals did not exhibit any changes in body weight or metabolic rate.

Figure 2:
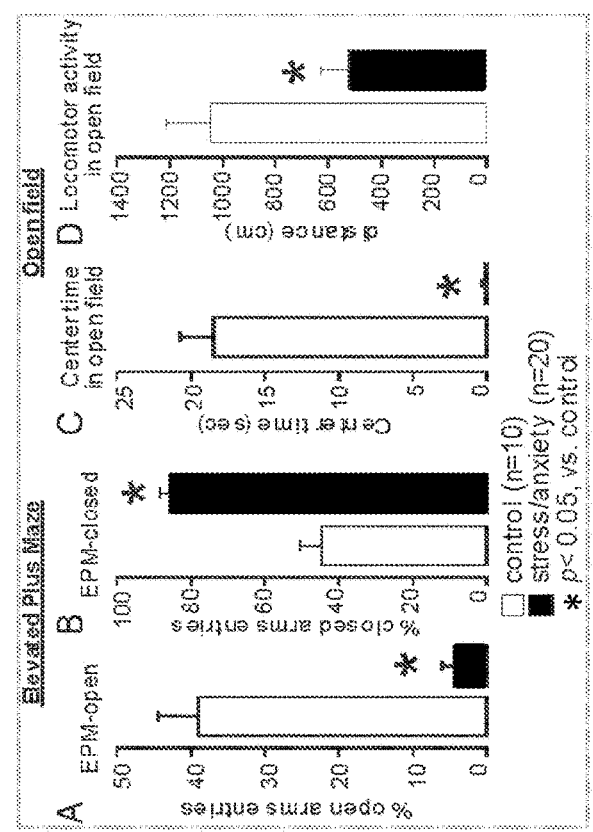
FIG. 2 shows that chronically stressed mice exhibited behavioral anxiety.

The effectiveness of DHM in the treatment of stress-induced hair loss was tested using two groups of eight week old C57BL/6J mice. Chronic stress was induced in the first group (n=20) by restraining each mouse in the test group for 3 hours per day for 21 consecutive days in a modified 50 ml clear polystyrene conical centrifuge tube with multiple air holes for ventilation. The second group of mice (n=10) remained undisturbed in their home cages (Fernandex-Vozmediano et al. (1994) "Contact dermatitis due to topical spironolactone." *Contact Dermatitis* 30: 118-9; Tresch, et al. (2011) "T cell-mediated acute localized exanthematous pustulosis caused by finasteride." *J Allergy Clin Immunol* 129: 589-94). The completion of the 21 day stress-induction cycle was followed by a two day withdrawal. The mice that were restrained in conical tubes exhibited diffuse hair loss, which was symptomatic of chronic stress (FIG. 1). The rodents' stress levels were also assessed via elevated plus maze (EPM) and open field test (OFT). EPM and OFT are behavioral tests that are commonly used to assess anxiety by measuring a mouse's locomotor activity and willingness to explore. When anxious, rodents naturally prefer enclosed dark spaces to opened brightly lit spaces. In the EPM test, individual mice from each group were placed on a plus-shaped apparatus that was raised from the floor and had two open and two enclosed arms. Within the context of EPM, anxiety-related behavior was measured by the degree to which a mouse avoided the unenclosed arms of the maze. As shown in FIG. 2A and FIG. 2B, the unstressed mice explored the open arms, whereas the chronically stressed mice avoided the open arms and restricted their movements to the closed arms. In OFT, each mouse was placed on an empty table surrounded by walls, and the mouse's movements and the time it spent moving were monitored. Within the context of OFT, anxiety-related behavior was measured by the degree to which a mouse avoided the open center and stayed close to the walls. As shown in FIG. 2C and FIG. 2D, the unstressed mice explored center of the table, whereas the chronically stressed mice avoided the center and remained in the corners. Taken together, the results show that the chronically stressed mice were observed to exhibit both hair loss and behaviors associated with anxiety.

Figure 3:
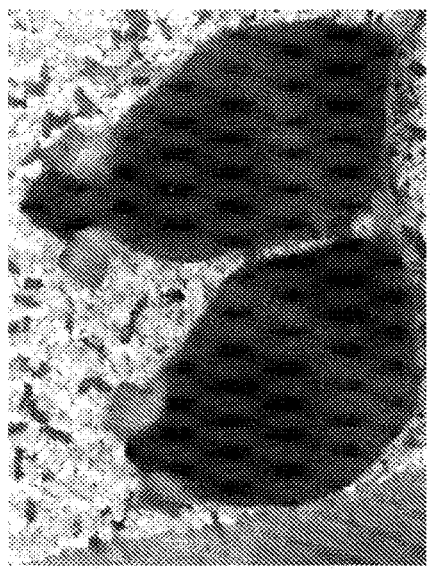
FIG. 3 shows the regrowth of hair on chronically stressed mice that underwent daily treatment with 1 μM dihydromyricetin for a period of 6 weeks.
Figure 4:
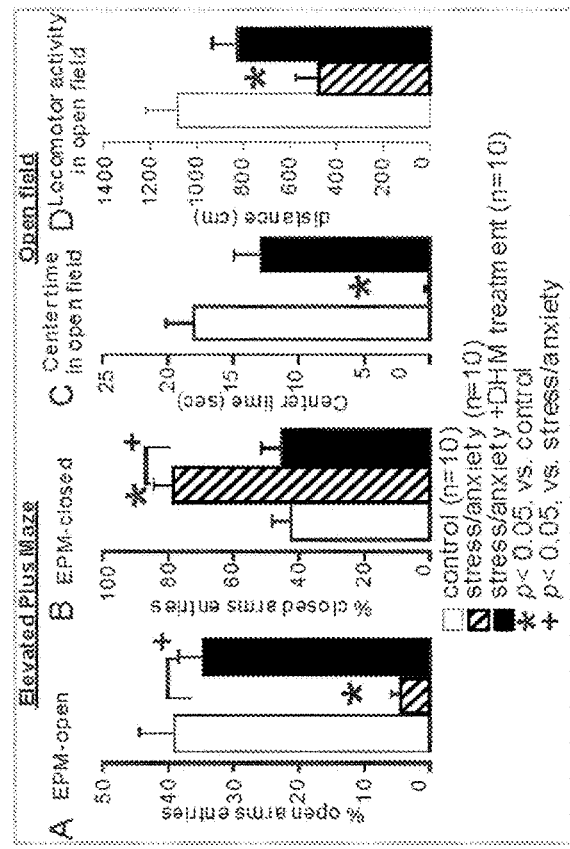
FIG. 4 shows that behavioral anxiety was reduced in chronically stressed mice that underwent daily treatment with 1 µM dihydromyricetin for a period of 6 weeks.

The chronically stressed mice were then divided into two groups: one group (n=10) was treatment with DHM (1 LM DHM in 1 oz. Vaseline) and the other group (n=10) was treated with Vaseline alone. Briefly, the Vaseline (i.e., with or without 1 μM DHM) was applied to a mouse's bald spots once per day for six weeks. Following treatment, hair regrowth was observed in mice treated with DHM (FIG. 3). EPM and OFT were repeated for all mice (i.e., unstressed; stressed and treated with DHM; and stressed and treated with Vaseline alone). As shown in FIG. 4A and FIG. 4B, the stressed mice treated with Vaseline+DHM were as willing to explore the open arms of the EPM apparatus as the unstressed control mice. In contrast, the stressed mice treated with Vaseline alone continued to avoid the open arms and confined their movements to the closed arms. Similar behavior patterns were observed in OPT. The stressed mice treated with Vaseline+DHM exhibited significantly increased locomotor activity and longer running distance comparable to those of unstressed mice, indicating recovery from chronic stress (FIGS. 4C and 4D). The stressed mice that were treated with Vaseline alone continued to exhibit anxiety-related behavior, such as the significant lack of motor activity (FIGS. 4C and 4D). Thus, both hair loss and behavioral anxiety were observed to be reversed in DHM-treated stressed mice.

Example 2: Effects of Dihydromyricetin (DHM) Treatment on Hair Growth

A total of 40 seven-week-old, wild type C57BL/6J male mice were used for the study. The mice were housed individually (one mouse/cage). The mice were randomly assigned to one of four treatment groups that contained 10 mice per group. The treatment groups included a vehicle control, a positive control (minoxidil 2%), DHM 5% (w/w-%), and DHM 10% (w/w-%).

The vehicle used for all treatment groups was a mixture of alcohol denat., propanediol, water, ethylhexylglycerin, and phenoxyethanol. The DHM used in the DHM treatment groups has a purity of 98%.

The vehicle control contained the following percentage concentrations (w/w-%): 20% alcohol denat., 50% propanediol, 29.5% water, and 0.5% ethylhexylglycerin and phenoxyethanol.

The minoxidil 2% positive control contained the following percentage concentrations (w/w-%): 20% alcohol denat., 2% minoxidil, 50% propanediol, 27.5% water, and 0.5% ethylhexylglycerin and phenoxyethanol.

The DHM 5% treatment contained the following percentage concentrations (w/w-%): 20% alcohol denat., 5% DHM, 50% propanediol, 24.5% water, and 0.5% ethylhexylglycerin and phenoxyethanol.

The DHM 10% treatment contained the following percentage concentrations (w/w-%): 20% alcohol denat., 10% DHM, 50% propanediol, 19.5% water, and 0.5% ethylhexylglycerin and phenoxyethanol.

The hair of the dorsal skin (2×5 cm) from every mouse was removed by clipping and topical application of calcium thioglycolate to depilate the clipped area. The next day, mice without visible wounds were used for the study. The mice received a daily topical application of 1 ml of their respective treatment per day. Hair regrowth was quantified by analyzing photographs that were taken of each mouse every 4 days after topical treatment for a total of 21 days (day 0, 4, 8, 12, 16, and 21). For each mouse, an area of 3 cm² of the back was analyzed. All experiments were continued for 21 days.

Evaluation the induction of anagen was performed on mice treated for 8 days using a simple grading system: 0=no anagen; 1=<50% of the total area on anagen; 2=>50% and <100% on anagen; and 3=100% of the total area on anagen. Evaluation of hair regrowth was performed on mice treated for 12 days, using a simple grading system: 0=no hair; 1=<50% of the total area covered with hair; 2=>50% and <100% of the total area covered with hair; and 3=100% of the total area covered with hair.

To determine whether anagen induction was promoted by DHM, C57BL/6 mice were used, as the dorsal hair of C57BL/6 mice is known to have a time-synchronized hair growth cycle. The shaved skin of C57BL/6 mice is pink, which then darkens along with anagen initiation. After 8 days of depilation, an area of black skin was clearly visible in the mice.

Figures 5, 6:
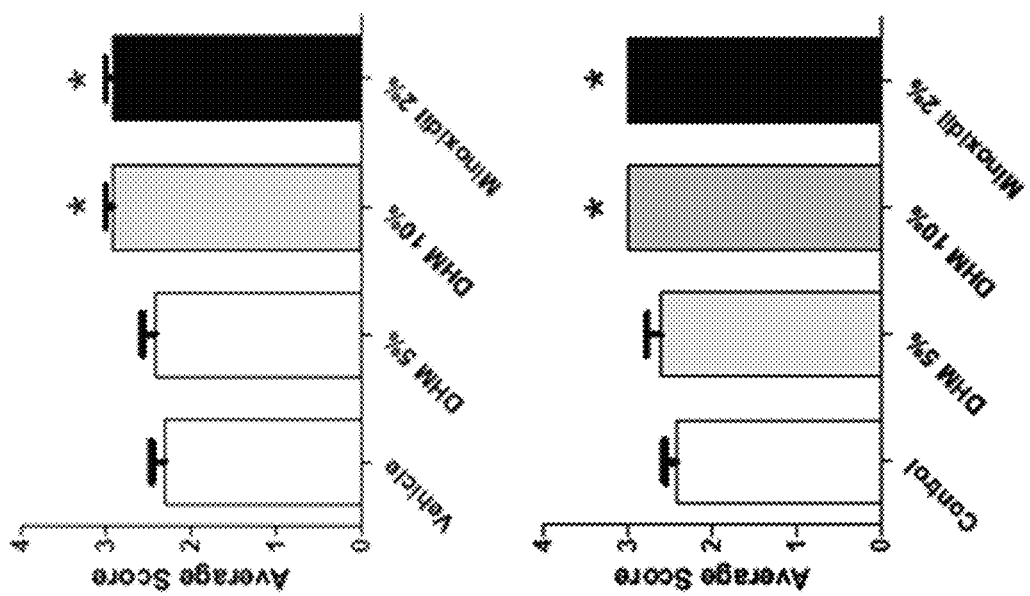
FIG. 5 shows the effects of vehicle (negative control), DHM 5%, DHM 10%, and positive control (Minoxidil 2%) on the induction of anagen on the skin of mice after 8 days of topical application. Statistical significance was evaluated with the non-parametric Kruskal-Walis test followed by Dunn's multiple comparison test. * P<0.05. N=10 per group.
FIG. 6 shows the effects of vehicle (negative control), DHM 5%, DHM 10%, and positive control (Minoxidil 2%) on hair growth of mice after 12 days of topical application. Statistical significance was evaluated with the non-parametric Kruskal-Walis test followed by Dunn's multiple comparison test. * P<0.05. N=10 per group.

As showed FIG. 5, treatment with DHM 10% was significantly different to treatment with the vehicle control, and similar to treatment with the positive control (minoxidil 2%) in the induction of anagen. Treatment with DHM 10% also showed a statistically significant increase in hair regrowth as compared to treatment with the vehicle control (FIG. 6). The results of treatment with DHM 10% were also similar to the effect observed with the minoxidil 2% positive control (FIG. 6).

What is claimed is:

1. A method for treating hair loss or inducing hair growth in an individual who has telogen effluvium (TE) or alopecia areata comprising applying an effective amount of a dihydromyricetin compound to scalp of an individual, wherein the dihydromyricetin compound is of formula (I):

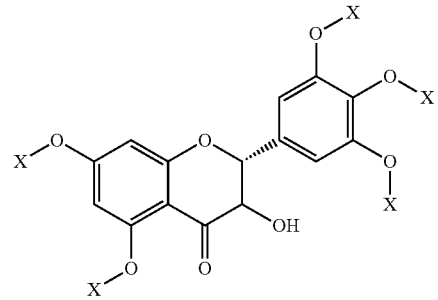

wherein each X is independently selected from hydrogen, alkyl, substituted alkyl, alkenyl, substituted alkenyl, halo, alkoxyl, heteroalkyl, substituted heteroalkyl, heteroalkenyl, or substituted heteroalkenyl;

wherein said dihydromyricetin compound is synthetic or is purified from a whole plant or a plant tissue of *Hovenia dulcis*; and wherein X is independently selected from the group consisting of —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —CH$_2$C(CH$_3$)$_2$CH$_3$, —C(CH$_3$)$_2$CH$_2$CH$_3$, —CH$_2$CH$_2$CH(CH$_3$)$_2$, —CH$_2$CH$_2$CH$_2$CH$_2$CH$_2$CH$_3$, —CH$_2$C(CH$_3$)$_2$CH$_2$CH$_3$, —CH$_2$CH$_2$C(CH$_3$)$_2$CH$_3$, —CH$_2$CH$_2$CH$_2$CH(CH$_3$)$_2$, —CH$_2$CH(CH$_2$CH$_3$)CH$_2$CH$_3$, —CH$_2$CH$_2$OCH$_3$, —CH$_2$CH$_2$CH$_2$OCH$_3$, —CH$_2$CH$_2$CH$_2$OCH$_2$CH$_3$, and —CH$_2$CH$_2$CH$_2$OCH$_2$CH$_3$.

2. The method of claim 1, wherein said dihydromyricetin compound is provided in a hair product.

3. The method of claim 2, wherein the hair product is a shampoo, a conditioner, or a hair spray.

4. The method of claim 2, wherein said dihydromyricetin compound in the hair product is in a concentration of at least about 5% (w/v-%) or at least about 5% (w/w-%).

5. The method of claim 2, wherein said dihydromyricetin compound in the hair product is in a concentration of at least about 10% (w/v-%) or at least about 10% (w/w-%).

6. The method of claim 2, wherein said dihydromyricetin compound in the hair product is in a concentration of about 0.01 µM to about 250 µM.

7. The method of claim 6, wherein said dihydromyricetin compound in the hair product is in a concentration of about 0.5 µM to about 10 µM.

* * * * *